United States Patent
Dan

(10) Patent No.: US 7,766,927 B2
(45) Date of Patent: Aug. 3, 2010

(54) SURGICAL TOOL AND METHOD FOR EXTRACTING TISSUE FROM WALL OF AN ORGAN

(75) Inventor: Jacob Dan, Hod Hasharon (IL)

(73) Assignee: D.O.T. Dan Opthalmic Technologies Ltd., Hod Hasharon (IL)

( * ) Notice: Subject to any disclaimer, the term of this patent is extended or adjusted under 35 U.S.C. 154(b) by 1121 days.

(21) Appl. No.: 11/382,271

(22) Filed: May 9, 2006

(65) Prior Publication Data

US 2006/0229648 A1    Oct. 12, 2006

Related U.S. Application Data

(62) Division of application No. 10/135,365, filed on May 1, 2002, now Pat. No. 7,041,114.

(51) Int. Cl.
*A61F 9/00* (2006.01)
*A61B 17/50* (2006.01)

(52) U.S. Cl. ........................ 606/166; 606/131

(58) Field of Classification Search .............. 606/131, 606/132, 161, 166, 167, 172; 30/57, 186, 30/330

See application file for complete search history.

(56) References Cited

U.S. PATENT DOCUMENTS 4,665,915 A * 5/1987 Grollimund .............. 606/132
6,440,143 B2 * 8/2002 Kasten ..................... 606/132

* cited by examiner

*Primary Examiner*—Julian W Woo
(74) *Attorney, Agent, or Firm*—Professional Patent Solutions Ltd.; Vladimir Sherman

(57) ABSTRACT

The present invention is concerned with methods and equipment for the treatment of the eye and more particularly with an instrument to increase eye filtration and treat glaucoma. The instrument is surgical tool operated entirely by the surgeon's hands and is composed of a hand-piece and an eye-penetrating intraocular segment each having two opponent and reciprocally operating fork-like arms and blade-sharp leaves, respectively. The eye-penetrating segment is a rigid embodiment of a size to create a limbus-pointing tunnel in the cornea, penetrate the eye of a patient through a water tight incision and, in a five step dissect and extract procedure, remove from within the eye a trabecular tissue block leaving the incision to self-seal by intraocular pressure. In the same "modus operandi", a sample tissue can be extracted from any other hollowed or parenchimatous organ.

22 Claims, 22 Drawing Sheets

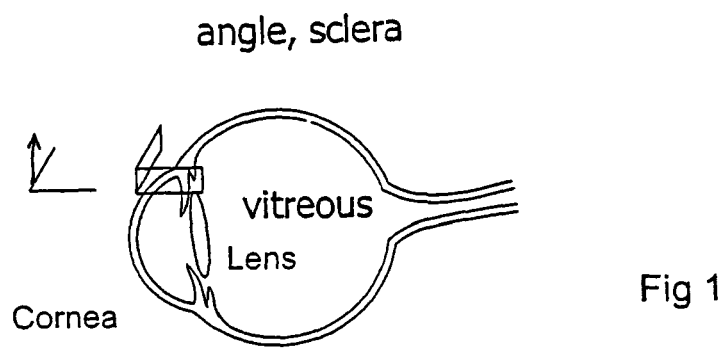
Fig 1
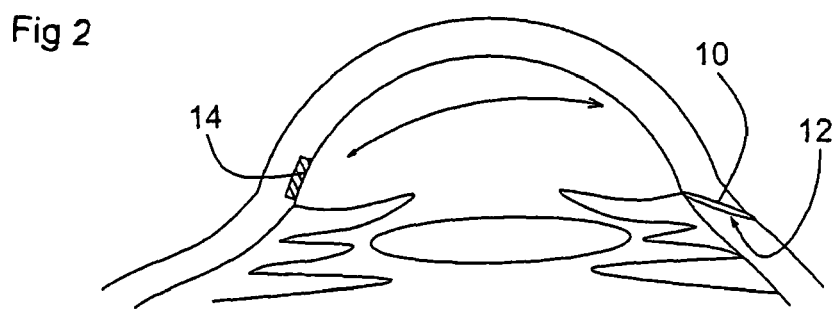
Fig 2
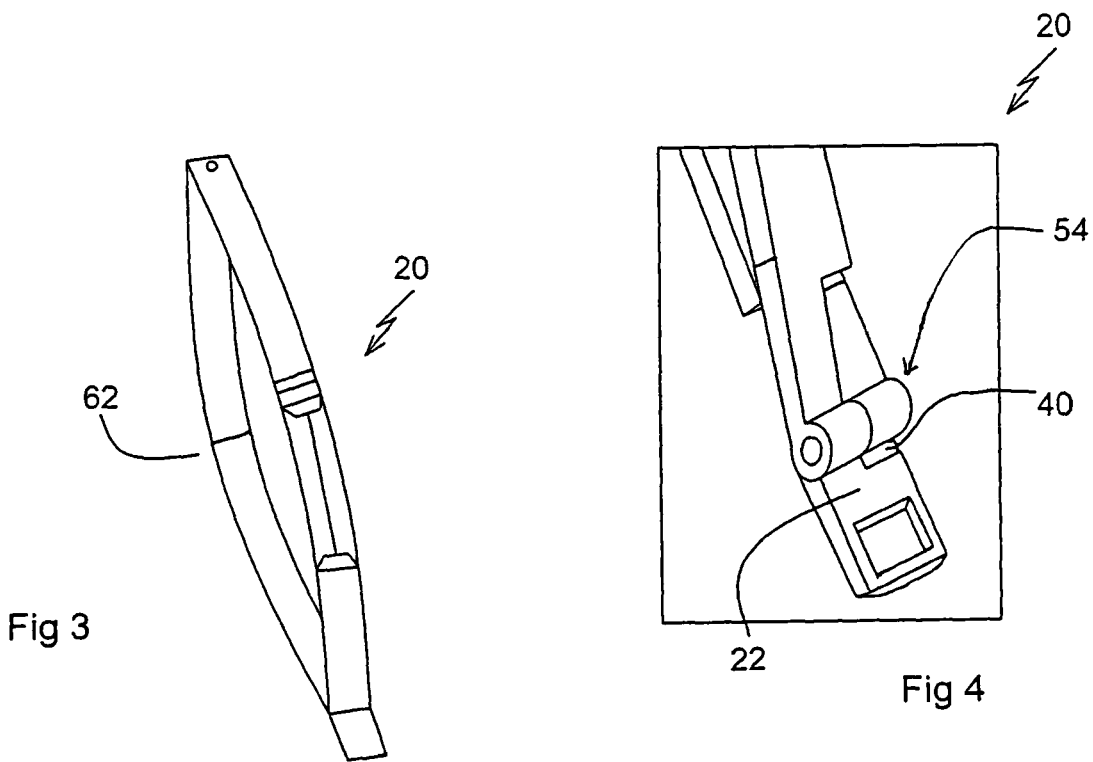
Fig 3
Fig 4

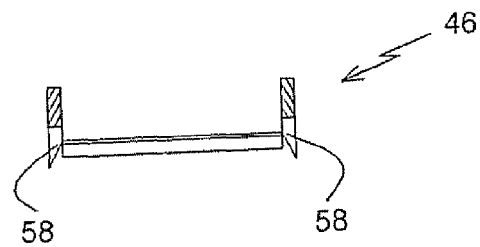
Fig 6E
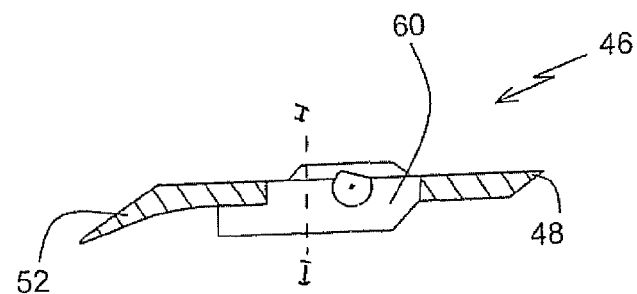
Fig 6DD
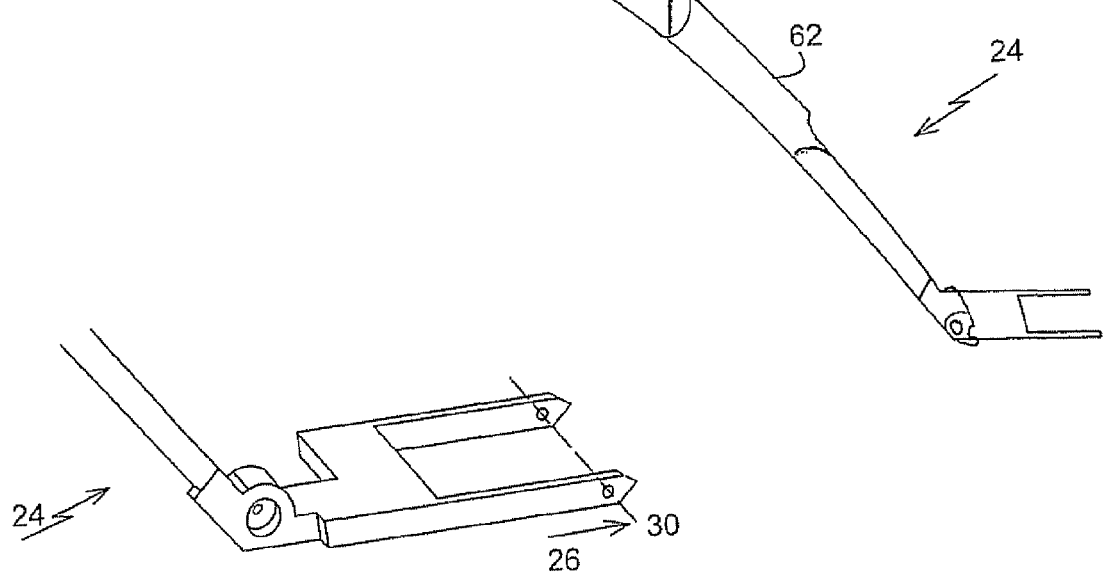
Fig 7B

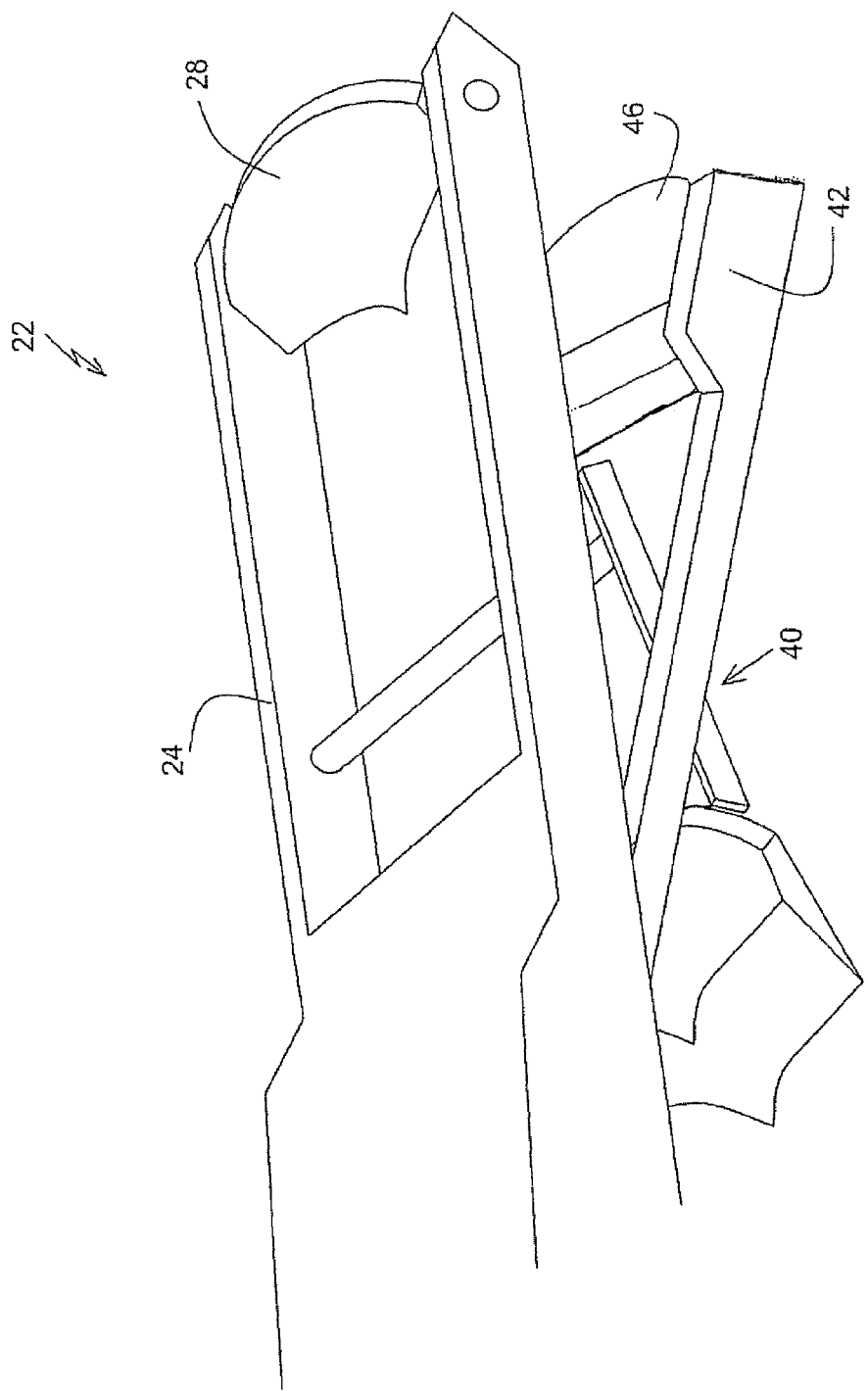

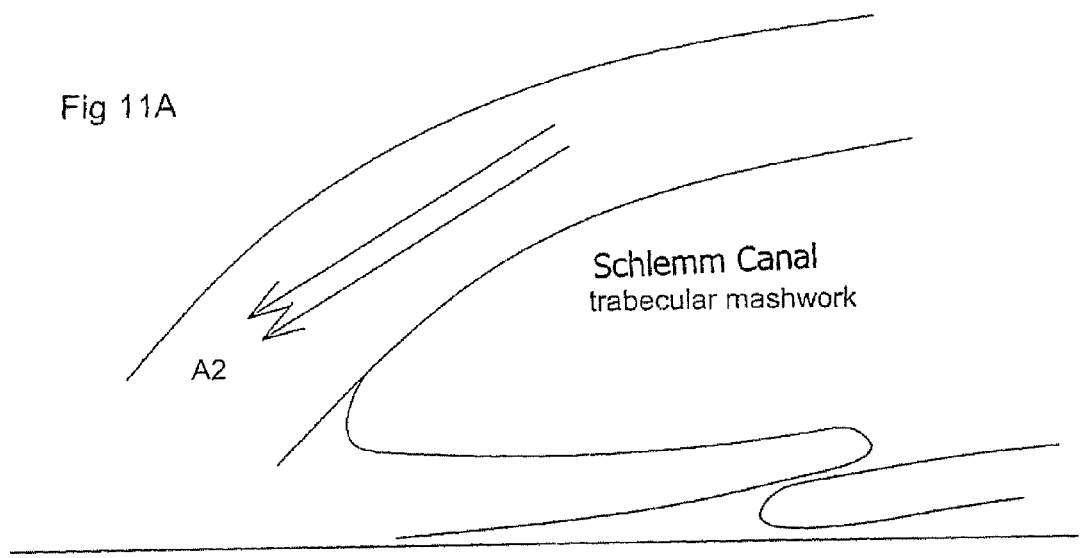
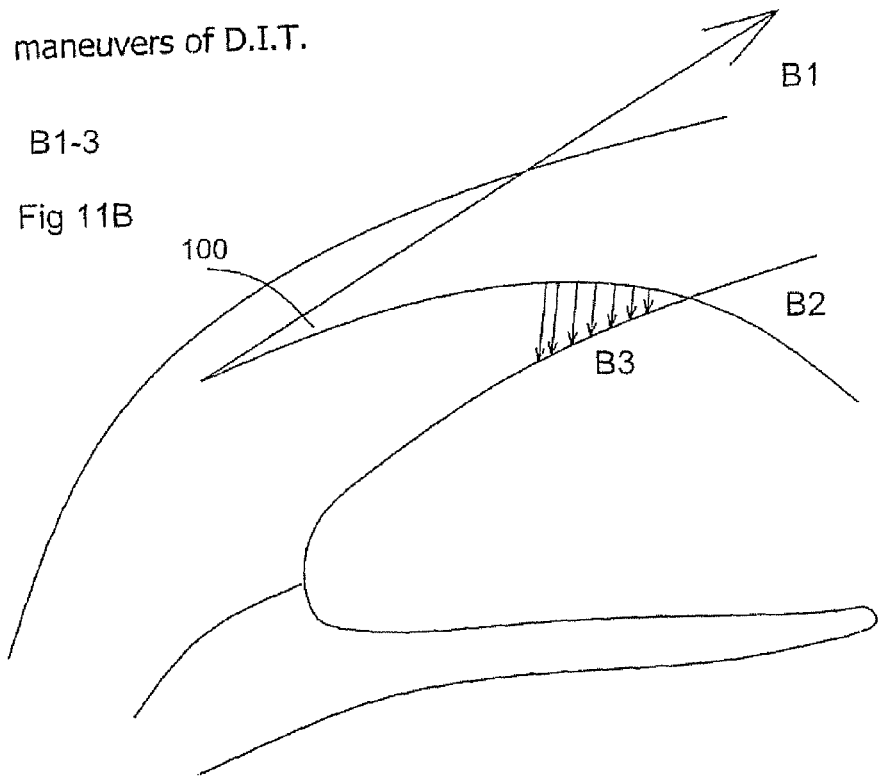

maneuver C1-2 maneuver D1-3 tissue block

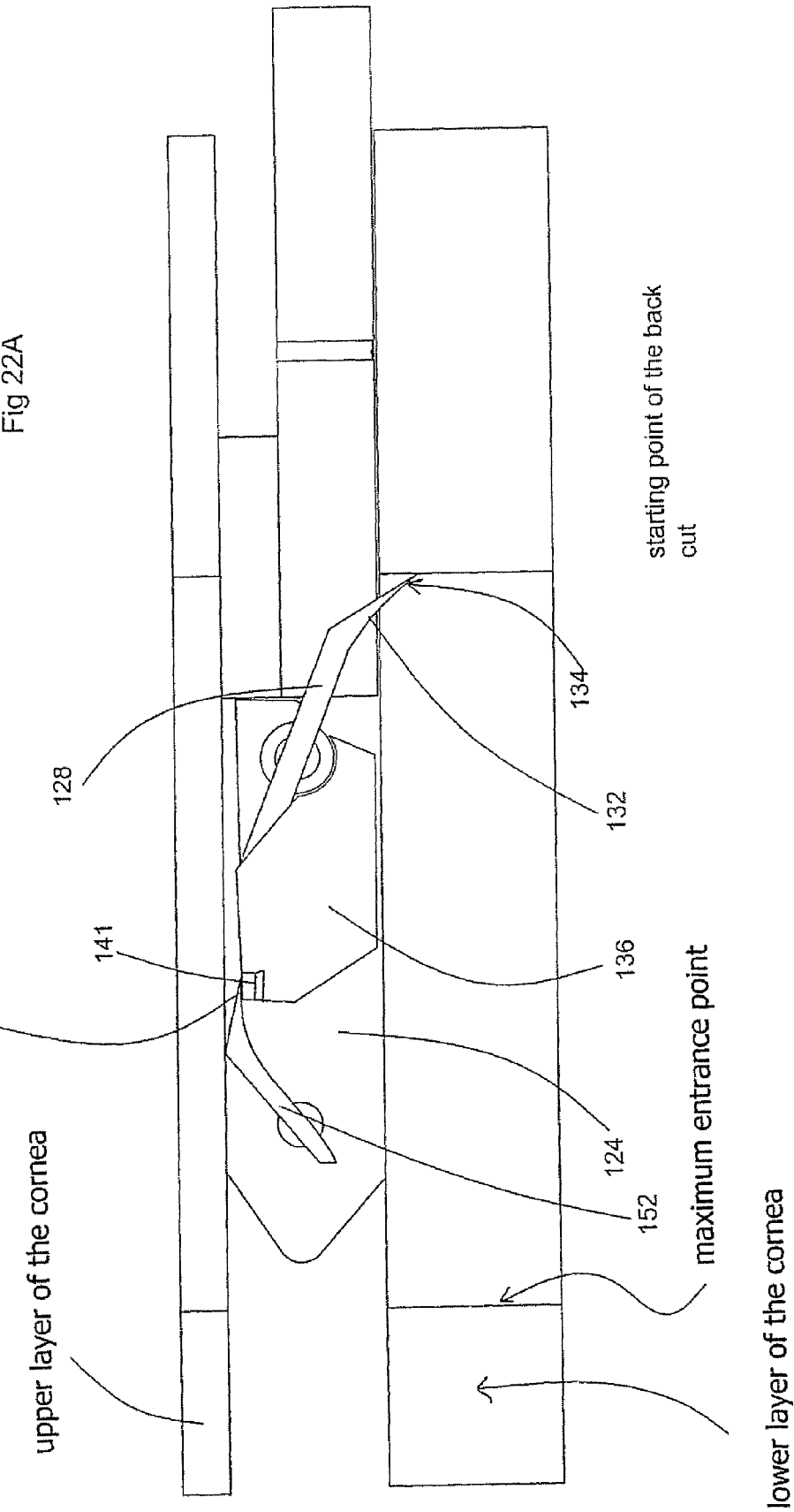

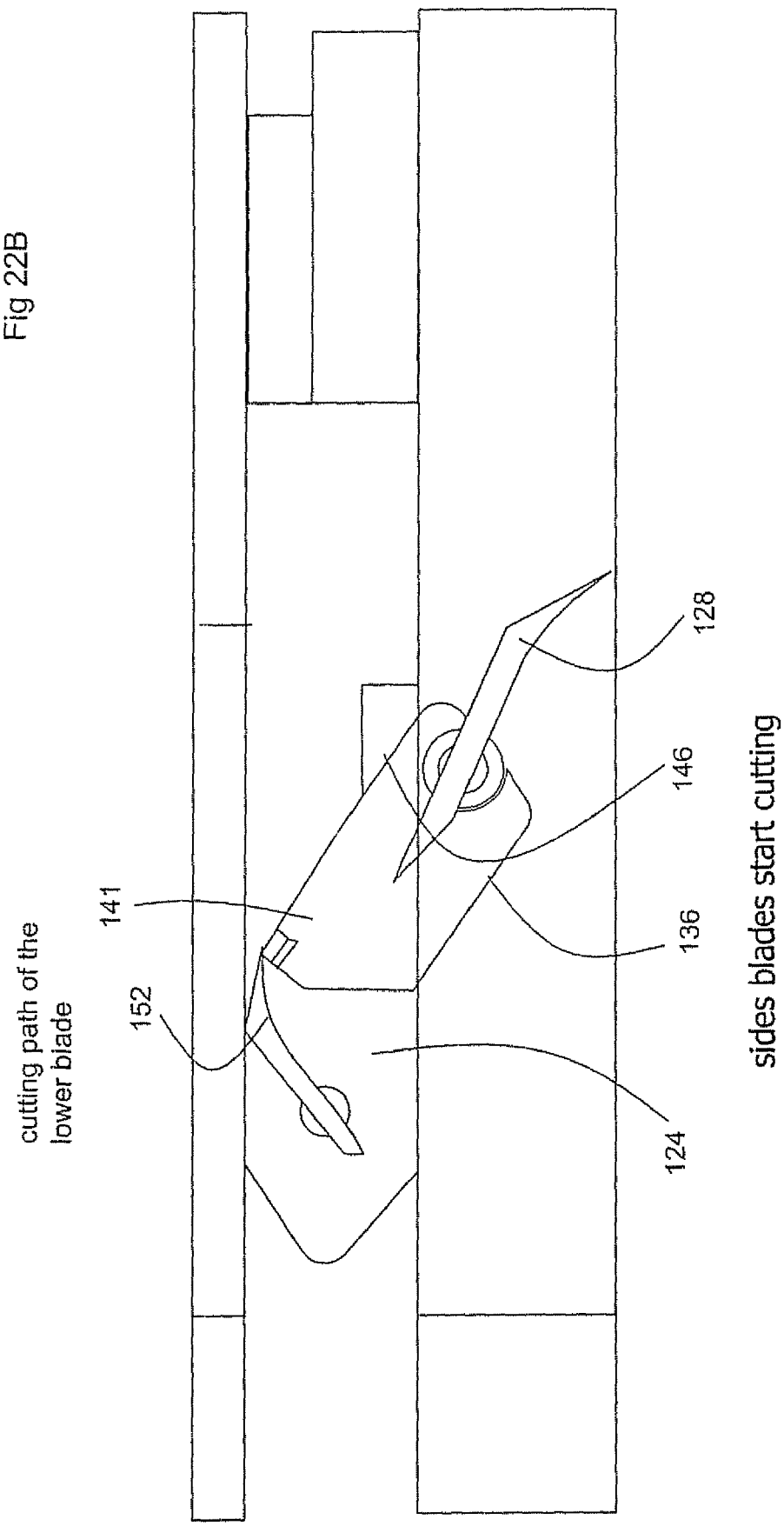

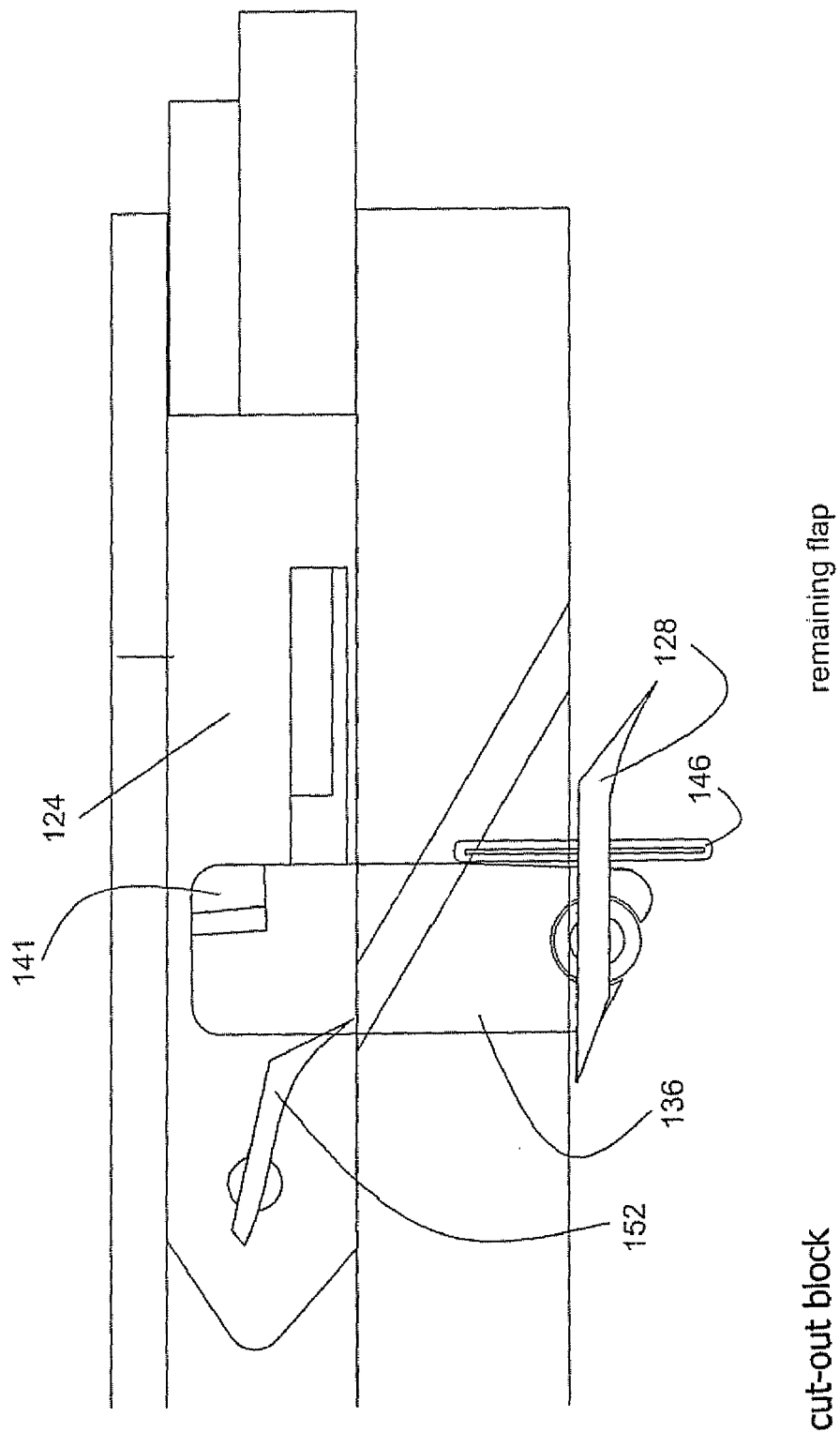

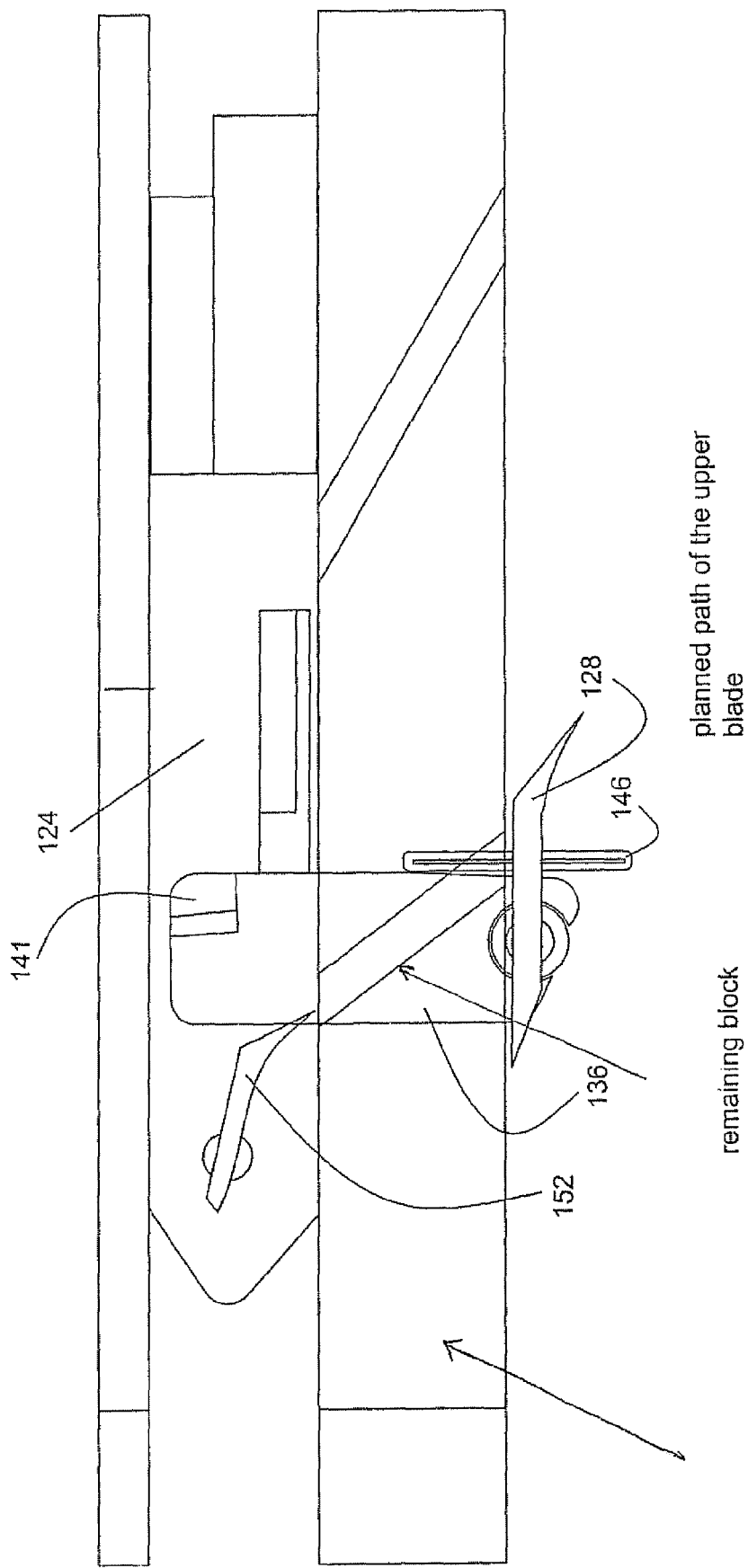

SURGICAL TOOL AND METHOD FOR EXTRACTING TISSUE FROM WALL OF AN ORGAN

This application is a Divisional of U.S. Ser. No. 10/135,365 filed May 1, 2002, now U.S. Pat. No. 7,041,114.

FIELD AND BACKGROUND OF THE INVENTION

The present invention relates to surgical tools and methods and, in particular, it concerns a surgical tool and corresponding method for extracting tissue from wall of an organ. The tool and method are particularly suited to procedures for lowering intraocular pressure.

Glaucoma is a disease in which intraocular pressure is a causative risk factor. It affects significant numbers of our population. The treatment of glaucoma is usually medicinal to lower the intraocular pressure. However, medications often fail to control some forms of glaucoma. When further treatment is required, a microsurgical operative procedure is performed.

Conventional surgical techniques for intraocular pressure reduction approach the tissue in the angle of the eye through the conjunctiva. The procedure involves constructing a fistula or opening in the tissue wall, or significant thinning of the tissue in the region of the angle of the eye (sclerokeratectomy or trabeculectomy, to enhance fluid (aqueous humor) flow from the internal portion of the eye through the newly formed opening. This surgery encounters many complications, ranging from loss of the volume and shape of the eye when the fistula is too large through to formation of scar tissue which seals down the fistula. The latter requires peri-operative application or injection of anti-metabolites, harboring a significant risk of bleeding, infections, wound leaks, buttonholing or penetrating vital tissues.

A corneal approach for surgical treatment of glaucoma has been proposed by J. E. Cairns ("Clear-Cornea Trabeculectomy", *Trans Ophthalmol Soc* UK 1985; 104:142-5) and by R. B. Keillor et al. ("Twenty-Two Cases of Clear Cornea Trabeculectomy", *Australian and New Zealand Journal of Ophthalmology* 1986: 14: 339-342). While this approach should theoretically offer advantages of minimizing complications due to damage to the conjunctiva, in practice, the results have been poor, primarily due to complications associated with the typically large corneal incision.

There is therefore a need for tools and methods for reliably removing a block of tissue from the region of the angle of the eye, including at least some trabecular tissue, without the complications resulting from damage to the conjunctiva. It would similarly be useful to provide a tool and method for extracting a tissue block from the wall of a hollow organ.

SUMMARY OF THE INVENTION

The present invention is a tool and method for extracting a tissue block from the wall of a hollow organ.

A method for extracting a tissue block from the angle of an eye, the method comprising: (a) forming a first elongated slit of substantially constant width entering at a peripheral region of the cornea, the first elongated slit providing a face of a self-sealing flap having a terminal angle of no more than 25°; (b) employing a tool inserted via the first elongated slit to the limbus underlying the conjunctiva to form a plurality of additional slits so as to define the tissue block; and (c) withdrawing the tissue block along the first elongated slit such that the first elongated slit is temporarily elastically deformed to allow passage of the tissue block and is then sealed by the self-sealing flap.

According to a further feature of the present invention, a second undercut slit is formed from a first position along the first elongated slit so as to further define the self-sealing flap.

According to a further feature of the present invention, the plurality of additional slits includes a second undercut slit from a first position along the first elongated slit so as to further define the self-sealing flap and so as to form at least a proximal cut of the tissue block.

According to a further feature of the present invention, the plurality of additional slits further includes a pair of side cuts below the first elongated slit so as to define sides of the tissue block.

According to a further feature of the present invention, the plurality of additional slits further includes a lower slit extending into the angle of the eye so as to at least partially define a lower side of the tissue block.

According to a further feature of the present invention, the plurality of additional slits further includes a third slit from a second position along the first elongated slit distal to the first position so as to form at least a distal cut of the tissue block.

According to a further feature of the present invention, the first elongated slit, the second undercut slit, the third slit and the side cuts are all performed by a manually operated mechanical tool inserted along the first elongated slit.

According to a further feature of the present invention, the first elongated slit extends at a maximum depth sufficiently small to render an instrument inserted therein visible through overlying tissue.

According to a further feature of the present invention, the substantially constant width of the first elongated slit is less than 5 mm.

There is also provided according to the teachings of the present invention, a method for extracting a tissue block from the wall of a hollow organ and forming a self-sealing flap in tissue of the wall, the method comprising: (a) forming a first elongated slit of substantially constant width extending from an outer surface of the wall into the wall, the first elongated slit forming a face of a self-sealing flap; (b) forming a plurality of additional slits so as to define the tissue block, the plurality of additional slits including: (i) a second undercut slit from a first position along the first elongated slit so as to further define the self-sealing flap so as to form a terminal angle of no more than 25°, the second undercut slit additionally forming at least a proximal cut of the tissue block, (ii) a pair of side cuts below the first elongated slit so as to define sides of the tissue block, and (iii) a third slit from a second position along the first elongated slit distal to the first position so as to form at least a distal cut of the tissue block; and (iv) withdrawing the tissue block along the first elongated slit such that the first elongated slit is temporarily elastically deformed to allow passage of the tissue block and is then sealed by the self-sealing flap.

According to a further feature of the present invention, the first elongated slit, the second undercut slit, the third slit and the side cuts are all performed by a manually operated mechanical tool inserted along the first elongated slit.

According to a further feature of the present invention, the plurality of additional slits further includes a lower slit so as to at least partially define a lower face of the tissue block.

There is also provided according to the teachings of the present invention, a surgical tool for forming a self-sealing flap in tissue of a wall of a hollow organ during a procedure for extracting a tissue block from the wall, the surgical tool comprising a tool head including: (a) an elongated support element having a direction of elongation and configured for insertion along a first slit parallel to the direction of elongation into the tissue of the wall; and (b) a blade element pivotally mounted on the support element so as to be pivotable about an axis perpendicular to the direction of elongation, the blade element including a rear blade with at least one deflecting feature configured for forming a second slit diverging from the first slit during withdrawal of the tool along the first slit, thereby forming a self-sealing flap in the tissue of the wall.

According to a further feature of the present invention, a plane passing through the support element parallel to both the direction of elongation and the axis is referred to as a tool plane, and wherein the blade element is mounted on the support element via a lever mechanism, the lever mechanism being configured to allow displacement of the blade element from an in-plane position in which the axis lies substantially within the tool plane to an out-of-plane position in which the axis is displaced so as to be parallel to, but removed from, the tool plane.

According to a further feature of the present invention, the lever mechanism includes a pair of lever arms each having a first end pivotally engaged with the support element and a second end pivotally engaged with the blade element.

According to a further feature of the present invention, the lever arms are configured such that, when the blade element assumes the out-of-plane position, at least part of each of the lever arms presents a blade edge extending substantially perpendicular to the tool plane and oriented for cutting parallel to the direction of elongation.

According to a further feature of the present invention, the lever mechanism further includes a lock element configured to retain the blade element in the out-of-plane position.

According to a further feature of the present invention, the blade element has a substantially planar upper surface, the lever mechanism further including a resilient biasing element deployed such that, when the blade element assumes the out-of-plane position, the biasing element biases the blade element to a position with the upper surface substantially parallel to the tool plane.

According to a further feature of the present invention, the blade element further includes a front blade configured for cutting a slit parallel to the tool plane during advancing of the tool along the first slit.

According to a further feature of the present invention, the blade element is referred to as the first blade element, and wherein the axis is referred to as the first axis, the tool head further including a second blade element pivotally mounted on the support element distally with respect to the first blade element, the second blade element being pivotable about a second axis parallel to the first axis, the second blade element including a rear blade with at least one deflecting feature configured for forming an additional slit diverging from the first slit during withdrawal of the tool along the first slit.

According to a further feature of the present invention, the lever mechanism further includes a retention element deployed such that, when the blade element assumes the in-plane position, the retention element abuts a surface of the second blade element so as to limit pivotal movement of the second blade element about the second axis and, when the blade element assumes the out-of-plane position, the retention element is removed from the second blade element so as not to limit pivotal movement of the second blade element about the second axis.

According to a further feature of the present invention, the elongated support element includes a fork portion formed with two projecting arms, the blade element being mounted between the projecting arms.

According to a further feature of the present invention, a distal portion of each of the projecting arms is formed as a blade parallel to the direction of elongation.

According to a further feature of the present invention, the blade element further includes a pair of side blades extending along a majority of a length between the front blade and the rear blade in a direction substantially perpendicular to the axis.

According to a further feature of the present invention, the blade element further includes an opening substantially circumscribed by the front blade, the rear blade and the pair of side blades.

According to a further feature of the present invention, there is also provided a blade control assembly including at least one abutment element mechanically interconnected with the elongated support element so as to be movable relative to the elongated support element between a closed position in which the at least one abutment element abuts the blade element so as to restrain pivotal movement of the blade element and an open position in which the abutment element is removed from the blade element so as to allow pivotal movement of the blade element.

According to a further feature of the present invention, the at least one abutment element is implemented as a second blade assembly including: (a) a second elongated support element having a second direction of elongation; and (b) a second blade element pivotally mounted on the second support element so as to be pivotable about a second axis perpendicular to the second direction of elongation.

According to a further feature of the present invention, the second blade element includes a second front blade configured for cutting a primary slit parallel to the second axis during advancing of the tool into the tissue of the wall, and a second rear blade with at least one deflecting feature configured for forming a secondary slit diverging from the primary slit during withdrawal of the tool along the first slit.

According to a further feature of the present invention, the second blade element is restrained from pivotal movement when the second blade assembly assumes the closed position.

According to a further feature of the present invention, the second blade assembly is resiliently biased towards the open position.

There is also provided according to the teachings of the present invention, a surgical tool for forming a self-sealing flap in tissue of a wall of a hollow organ and extracting a tissue block from the wall, the surgical tool comprising: (a) a first blade assembly including: (i) a first elongated support element having a first direction of elongation, and (ii) a first blade element pivotally mounted on the first support element so as to be pivotable about a first axis perpendicular to the first direction of elongation, the first blade element including a first front blade configured for cutting a first forward slit parallel to the first axis during advancing of the tool, and a first rear blade with at least one deflecting feature configured for forming a first reverse slit diverging from the first forward slit during withdrawal of the tool along the first forward slit; (b) a second blade assembly including: (i) a second elongated support element having a second direction of elongation, and (ii) a second blade element pivotally mounted on the second support element so as to be pivotable about a second axis perpendicular to the second direction of elongation, the second blade element including a second front blade configured for cutting a second forward slit parallel to the second axis during advancing of the tool, and a second rear blade with at least one deflecting feature configured for forming a second reverse slit diverging from the second forward slit during withdrawal of the tool along the second forward slit; and (c) a mechanical linkage interconnecting between the first elongated support element and the second elongated support element so as to define a range of relative movement between a closed position in which the first blade assembly is closed against the second blade assembly and an open position in which the first blade assembly and the second blade assembly are spaced apart.

According to a further feature of the present invention, the first blade assembly and the second blade assembly are configured such that, when in the closed position, the first blade element and the second blade element are restrained against pivotal movement.

According to a further feature of the present invention, each of the first elongated support element and the second elongated support element includes a fork portion formed with two projecting arms, the first and second blade elements being mounted between the projecting arms.

According to a further feature of the present invention, a distal portion of each of the projecting arms is formed as a blade parallel to the direction of elongation.

According to a further feature of the present invention, the blade element further includes a pair of side blades extending along a majority of a length between the front blade and the rear blade in a direction substantially perpendicular to the axis.

According to a further feature of the present invention, the blade element further includes an opening substantially circumscribed by the front blade, the rear blade and the pair of side blades.

BRIEF DESCRIPTION OF THE DRAWINGS

The invention is herein described, by way of example only, with reference to the accompanying drawings, wherein:

FIG. 1 is a schematic cross-sectional representation of the structure of an eye;

FIG. 2 is an enlarged schematic cross-sectional representation of a region around the angle of the eye;

FIG. 3 is an isometric view of a first preferred embodiment of a surgical tool, constructed and operative according to the teachings of the present invention, for forming a self-sealing flap in tissue of a wall of a hollow organ and extracting a tissue block from the wall;

FIG. 4 is an enlarged view of a distal portion of the tool of FIG. 3;

FIGS. 6A, 6B, 6C and 6D are upper isometric, lower isometric, top and side cross-sectional views, respectively, of a posterior blade element from the tool of FIG. 3;

FIG. 6E is a cross-section taken along the line I-I in FIG. 6D;

FIG. 7A is an isometric view of an upper support element for supporting the anterior blade element of FIGS. 5A-5C;

FIG. 7B is an enlarged isometric view of the distal portion of the upper support element of FIG. 7A;

FIGS. 10A and 10B are isometric views of the distal portion of the tool of FIG. 3 in a closed state and an open state, respectively;

FIGS. 11A, 11B, 11C and 11D are schematic cross-sectional views of the angle of the eye illustrating a sequence of incisions used according to one preferred implementation of the method of the present invention;

FIGS. 22A-22D are a series of schematic side cross-sectional views illustrating the sequence of operation of the surgical tool of FIG. 14.

DESCRIPTION OF THE PREFERRED EMBODIMENTS

Figure 5B:
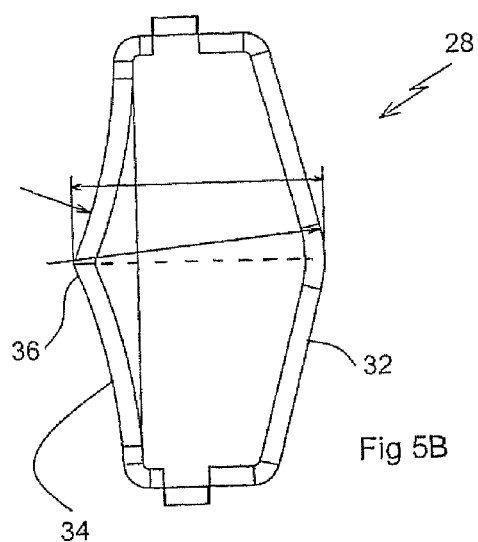
FIGS. 5A, 5B and 5C are isometric, top and rear views, respectively, of an anterior blade element from the tool of FIG. 3.
Figure 5A:
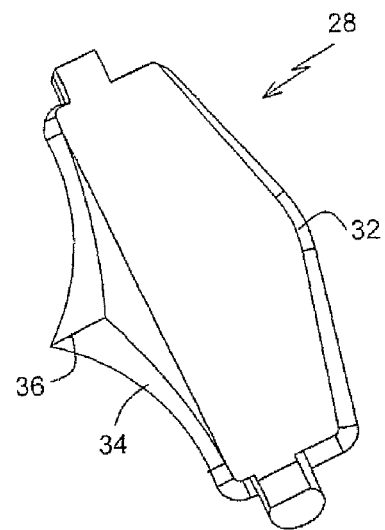
Figure 5C:
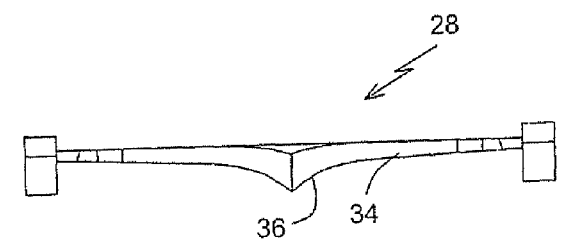
Figure 6A:
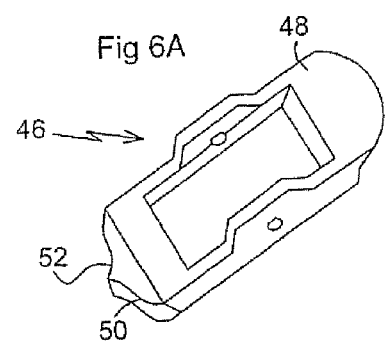
Figure 6C:
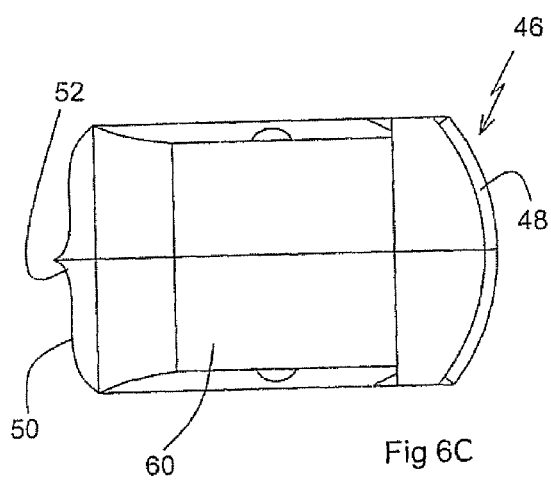
Figure 6B:
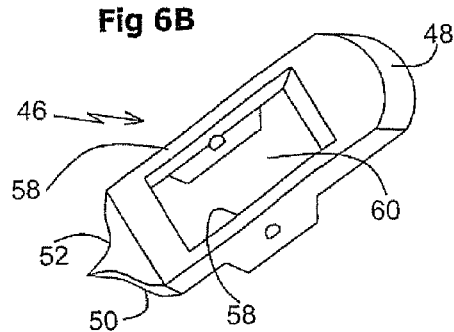
Figure 8A:
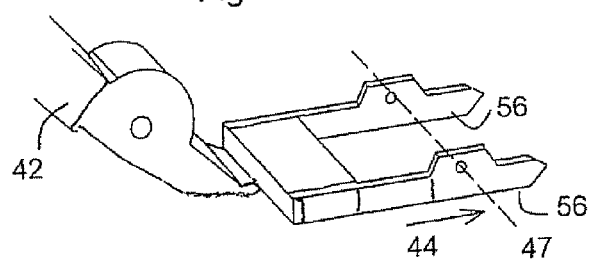
FIG. 8A is an isometric view of a lower support element for supporting the posterior blade element of FIGS. 6A-6E.
Figure 8B:
FIG. 8B is an enlarged isometric view of the distal portion of the lower support element of FIG. 8A.
Figure 9A:
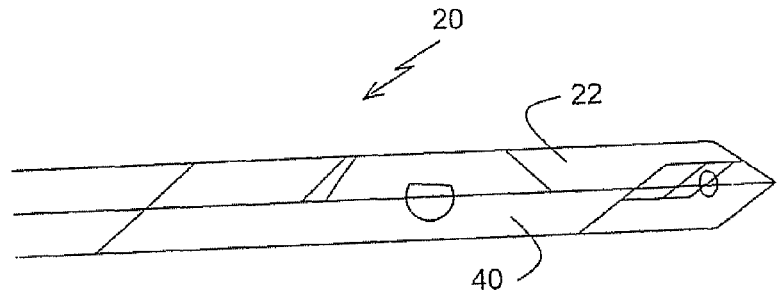
FIGS. 9A and 9B are side views of the distal portion of the tool of FIG. 3 in a closed state and an open state, respectively.
Figure 9B:
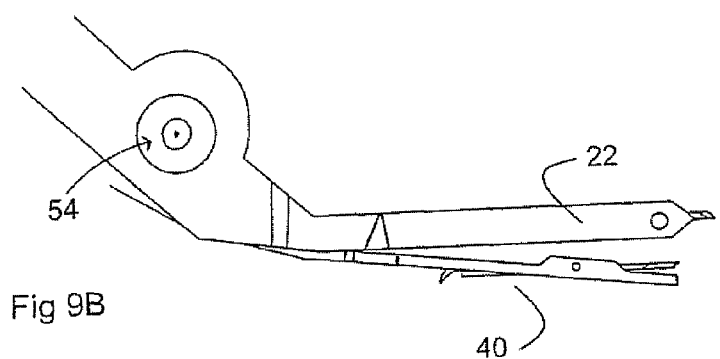
Figure 10A:
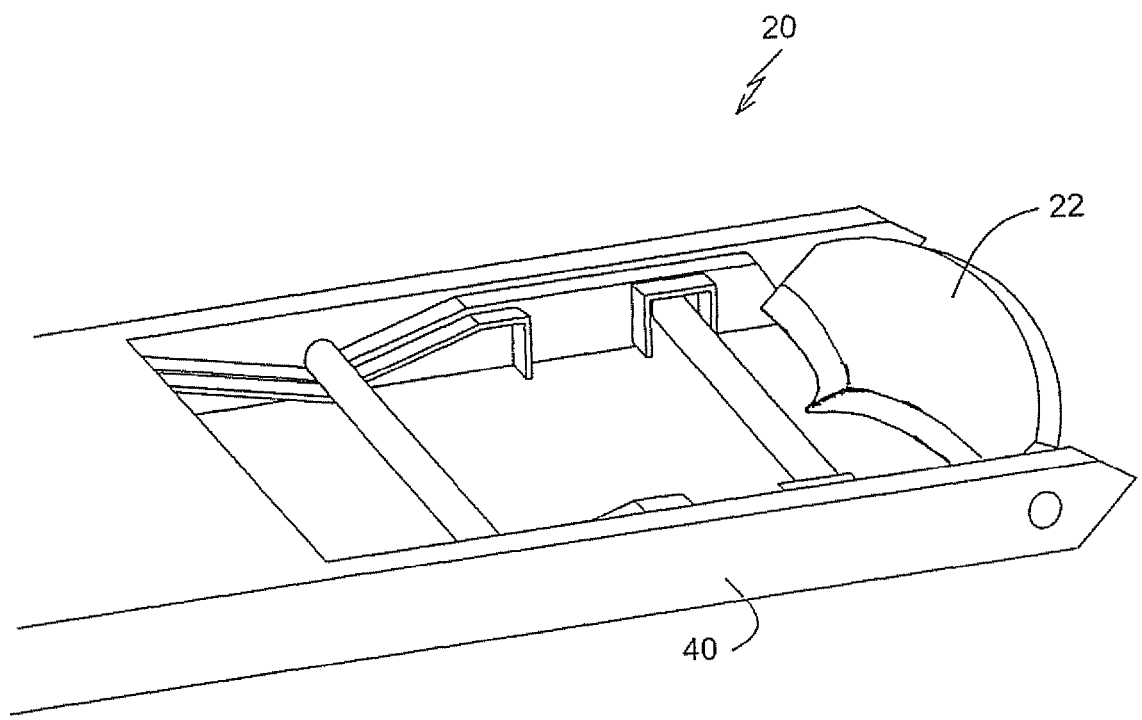

The present invention is a method for extracting a tissue block from the wall of a hollow organ and forming a self-sealing flap in tissue of the wall. Also provided is a preferred example of a surgical tool and a corresponding specific example of implementation of the method of the invention.

The principles and operation of surgical tools and methods according to the present invention may be better understood with reference to the drawings and the accompanying description.

Referring now to the drawings, FIG. 2, an enlarged view of a part of the eye shown in FIG. 1, shows the underlying principles of a surgical method for extracting a tissue block from the wall of a hollow organ and forming a self-sealing flap in tissue of the wall, particularly as applied to the eye. Thus, in general terms, the method includes forming an elongated slit 10 of substantially constant width extending from an outer surface of the wall into the wall, typically at a shallow angle, so as to at least partially define a self-sealing flap 12, forming a plurality of additional slits so as to define the tissue block 14, and withdrawing tissue block 14 along the elongated slit 10 such that the first elongated slit is temporarily elastically deformed to allow passage of the tissue block and is then sealed by the self-sealing flap 12.

Reference is made herein to a "self sealing flap". This term is used to refer to an inward-facing flap which has a small-angle edge positioned so as to tend to seal itself against the overlying tissue when exposed to fluid pressure from within the organ. In certain fields of surgery, for example ocular surgery, the use of a self-sealing flap is particularly valuable in avoiding the need for stitching of the incision after completion of the procedure. Preferred flap edge angles for self-sealing flaps are in the range of 15°-25°, and most preferably about 17°. It should be noted that the flap angle may be formed by a single shallow-angle cut together with the internal surface of the hollow organ, or by a first cut followed by a second "undercut" incision which defines the flap edge angle. The flap may be severed at its lateral sides but, more preferably, is left connected to lateral tissue which tends to return it to its natural closed position.

As mentioned, the method is believed to be of particular value as applied to the eye. In this case, the elongated slit 10 preferably enters at a peripheral region of the cornea so as to allow insertion of a tool towards the limbus to a position underlying the conjunctiva. By entering the eye through the non-vascular corneal tissue, all of the aforementioned complications associated with damage to the vascular tissue of the conjunctiva are avoided. At the same time, since the incision is configured with a self-sealing tissue flap, the slit closes immediately on completion of the procedure to form a watertight seal. This and other advantages of the method of the present invention will be better appreciated in view of the following description.

It should be noted that the method of the present invention as stated generally is not limited to implementation with any specific device or tool, or to any specific geometric relation between the location of entry into the eye and the location from which the tissue block is cut. Thus, for example, in the schematic example of FIG. 2, the entry slit 10 is shown near the periphery of the cornea on one side and the tissue block 14 is shown at the opposite side of the anterior chamber. Nevertheless, by way of a preferred example, the method will now be described with reference to specific implementations as performed by use of tools 20 and 120, constructed and operative according to the teachings of the present invention. Tool 20 and the corresponding method steps will be described, respectively, with reference to FIGS. 3-10B and 11A-13. Tool 120 and the corresponding method steps will be described, respectively, with reference to FIGS. 14-21 and 22A-22D.

Turning now to the features of tool 20, this is preferably based upon at least one, and preferably two, blade assemblies each including a blade element pivotally mounted on a support element so as to be pivotable about an axis perpendicular to a direction of elongation of the support element. In each case, the blade element includes a rear blade with at least one deflecting feature configured for forming a slit diverging from the path of insertion during withdrawal of the tool along a slit. In certain preferred cases, the blade element also includes a front blade configured for cutting forward during an advancing motion. The effect of this combination will be better understood from the following description with reference to the two preferred embodiments described herein. Specifically, a first preferred embodiment will be described with reference to FIGS. 3-13, while a second preferred embodiment will be described with reference to FIGS. 14-22.

Turning specifically to the first preferred implementation of surgical tool 20 shown in FIGS. 3, 4 and 9A-10B, and the corresponding components thereof shown in FIGS. 5A-8B, tool 20 here includes a first blade assembly 22 including a first elongated support element 24 (FIGS. 7A and 7B) having a first direction of elongation 26, and a first blade element 28 (FIGS. 5A-5C) pivotally mounted on first support element 24 so as to be pivotable about a first axis 30 perpendicular to direction of elongation 24. First blade element 28 includes a first front blade 32 configured for cutting a first forward slit parallel to the first axis during advancing of the tool, and a first rear blade 34 with at least one deflecting feature 36 configured for forming a reverse slit diverging from the first forward slit during withdrawal of the tool along the first forward slit. Deflecting feature 36, and other similar deflecting figures mentioned herein, are most simply implemented as a bent-over pointed extension of the blade as shown. Nevertheless, it will be clear to one ordinarily skilled in the art that various other forms of deflecting feature may readily be substituted for the form shown here.

Tool 20 further includes a second blade assembly 40 including a second elongated support element 42 (FIGS. 8A and 8B) having a second direction of elongation 44 and a second blade element 46 (FIGS. 6A-6E) pivotally mounted on second support element 42 so as to be pivotable about a second axis 47 perpendicular to the second direction of elongation 44. Second blade element 46 includes a second front blade 48 configured for cutting a second forward slit parallel to the second axis during advancing of the tool, and a second rear blade 50 with at least one deflecting feature 52 configured for forming a reverse slit diverging from a forward slit (typically the first forward slit formed by the first blade assembly 22) during withdrawal of the tool along the slit.

First elongated support element 24 and second elongated support element 42 are interconnected by a mechanical linkage 54 so as to define a range of relative movement between a closed position (FIGS. 9A and 10A) in which first blade assembly 22 is closed against second blade assembly 40 and an open position (FIGS. 9B and 10B) in which first blade assembly 22 and second blade assembly 42 are spaced apart. In the case illustrated here, elongated support elements 24 and 42 are integrally formed with handle portions 62 proximal to mechanical linkage 54. Tool 20 is preferably resiliently biased towards the open position of FIGS. 9B and 10B, optionally by a spring biasing of handle portions 62 such as is shown here. In this case, closing of the tool is performed manually by squeezing the handles together. Clearly, other actuation mechanisms known in the art may be used. Optionally, the actuation mechanism includes a self-locking configuration to selectively retain the tool in the closed position until released by the practitioner.

It should be appreciated that the structure of a single blade assembly 22 is a useful tool even if used alone, without the second blade assembly and mechanical linkage. Specifically, the structure may be inserted into tissue so that front blade 32 cuts an elongated slit alone which the assembly advances. Then, on withdrawal of the assembly, deflecting feature 36 lodges in the tissue of the slit and causes rear blade 34 to form a second undercut slit rearwardly diverging from the first elongated slit so as to at least partially define a self-sealing flap. Nevertheless, as will be explained, a preferred implementation of a tool including two blade assemblies with a mechanical linkage and various additional features to be described is believed to offer a particularly advantageous mode of operation for a surgical procedure, as will be detailed with reference to FIGS. 11A-11D and 12A-12E below.

Preferably, blade assemblies 22 and 40 are configured such that, when in the closed position, blade elements 28 and 46 are restrained against pivotal movement. In a basic implementation in which a single blade assembly is used, pivotal restraint may be achieved by providing a dedicated abutment element (not shown) mechanically interconnected with the elongated support element so as to be movable relative thereto. The abutment element is then selectively deployable so as to restrain or allow pivotal movement of the blade element.

In the preferred case shown here, the "abutment element" for each blade assembly is preferably provided by the opposing blade assembly. Specifically, the blade assemblies are configured here to provide direct abutment of the lower surface of blade element 28 with the upper surface of blade element 46, thereby locking both blade elements against pivotal movement when closed.

In a preferred implementation, elongated support elements 24 and 42 both include a fork portion formed with two projecting arms, the corresponding blade elements 28 and 46 being mounted between the projecting arms. In the case of first elongated support element 24, the extremities of the fork portion are here implemented as sharpened blade edges so that they cut together with front blade 32 during forward incision to form a slit. Optionally, the form of engagement between blade elements 28 and 46 and the respective fork portions may be shaped so as to limit rotation of the blade elements to a predetermined angular range, typically from the "straight" position to an angle of about 30°.

It should be noted in this context that the "direction of elongation" for each support element is taken to be the direction of elongation of the support portion of the element adjacent to the blade element. Thus, in this case, the direction of elongation for each support element is defined by the extensional direction of the projecting arms of the fork.

In the preferred embodiment shown here, both support element 42 and blade element 46 differ significantly from the corresponding elements of first blade assembly 22. Specifically, support element 42 is here formed with a distal portion of each of the projecting arms providing a downward facing blade edge 56 extending parallel to the direction of elongation. Blade element 46 is similarly formed with a pair of side blades 58 extending along a majority of a length between front blade 48 and rear blade 50 in a direction substantially perpendicular to axis 47. Front blade 48, rear blade 50 and pair of side blades 47 preferably substantially circumscribe an opening 60.

Turning now to FIGS. 11A-13, the operation of tool 20 and a corresponding preferred method of the present invention will now be described.

A shown in FIG. 11A, tool 20 is first inserted into the tissue at a shallow angle (preferably no more than about 25°) to form a first elongated slit $A_{1-2}$. At this stage, tool 20 is in its closed state as shown in FIG. 12A so that front blade 32 and sharpened extremities of the fork portion of first blade assembly 22 cut a flat slit along which the closed distal end of the tool advances. Slit $A_{1-2}$ is preferably formed to a maximum depth sufficiently small to render the tool visible through overlying tissue, and typically no more than about 0.2 mm. As a result of the form of tool 20, the slit exhibits a substantially constant width. For ocular applications, the total width of tool 20, and hence also of the first elongated slit, is preferably less than about 5 mm.

Next, tool 20 is drawn back along the first elongated slit while simultaneously being gently biased towards its open state. During this motion, deflecting feature 52 of second blade assembly 40 lodges in the wall of the first elongated slot and starts to form a second undercut slit $B_2$ from a first position along the first elongated slit so as to further define a self-sealing flap 100 (FIG. 11B). The form of deflecting feature 52 tends to guide rear blade 50 to form slit $B_2$ as an arcuate slit. At the same time, the sharpened side blades 58 which form a chord partially within the arcuate path, as well as blade portions 56 of the lower fork, start to cut side slits $B_3$. First blade assembly 22, biased upwards by the opening bias applied to tool 20, follows the path of the first elongated slit in reverse, designated $B_1$. The motion of tool 20 at this stage is shown in FIG. 12B.

Figure 12A:
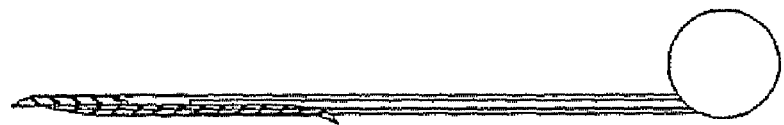
FIGS. 12A, 12B, 12C, 12D and 12E are schematic side view representations of a sequence of positions assumed by the tool of FIG. 3 during implementation of the method of FIGS. 11A-11D.
Figure 12B:
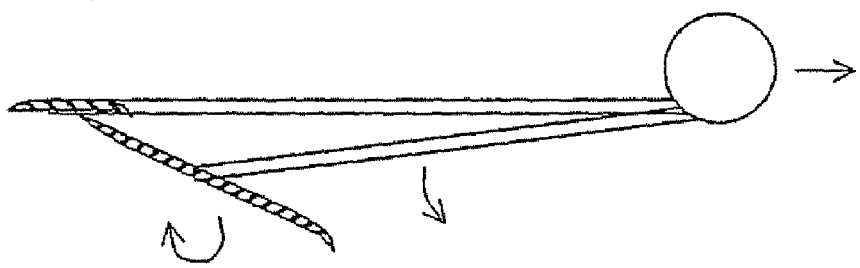
Figure 12C:
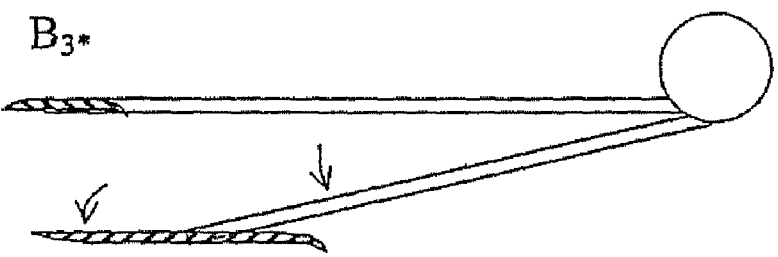

At the end of the withdrawing motion, after second blade element 46 penetrates the inner surface of the organ wall, the opening bias of the tool is further released to force the fork portion of second support element 42 inwards. This movement is accompanied by further cutting by blade portions 58 in direction $B_3$ to form a pair of side cuts below the first elongated slit, thereby defining sides of the tissue block. The corresponding tool motion is shown in FIG. 12C. This preferably brings the entirety of second blade element 40 to a position beyond the inner surface of the tissue wall.

Figure 11C:
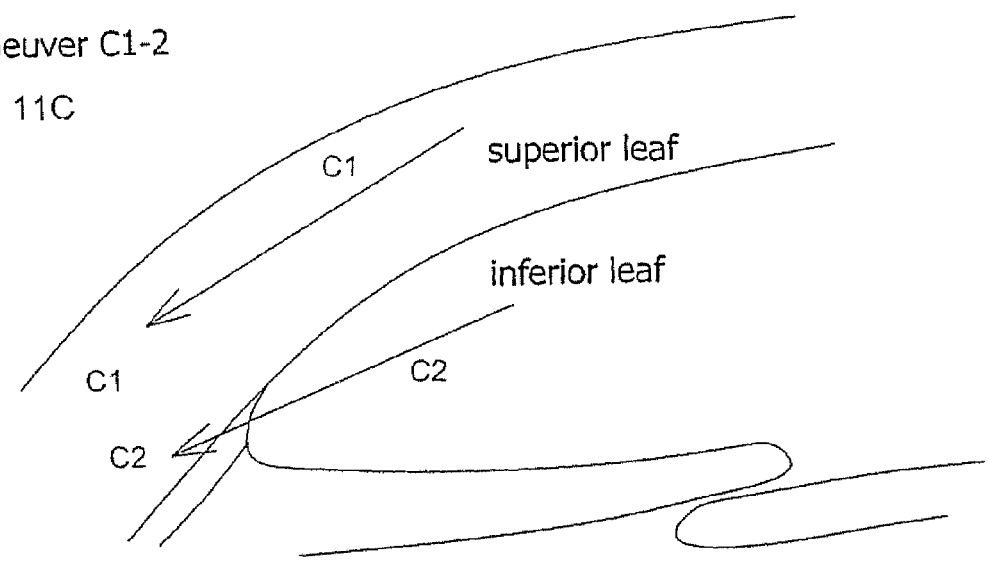
Figure 11D:
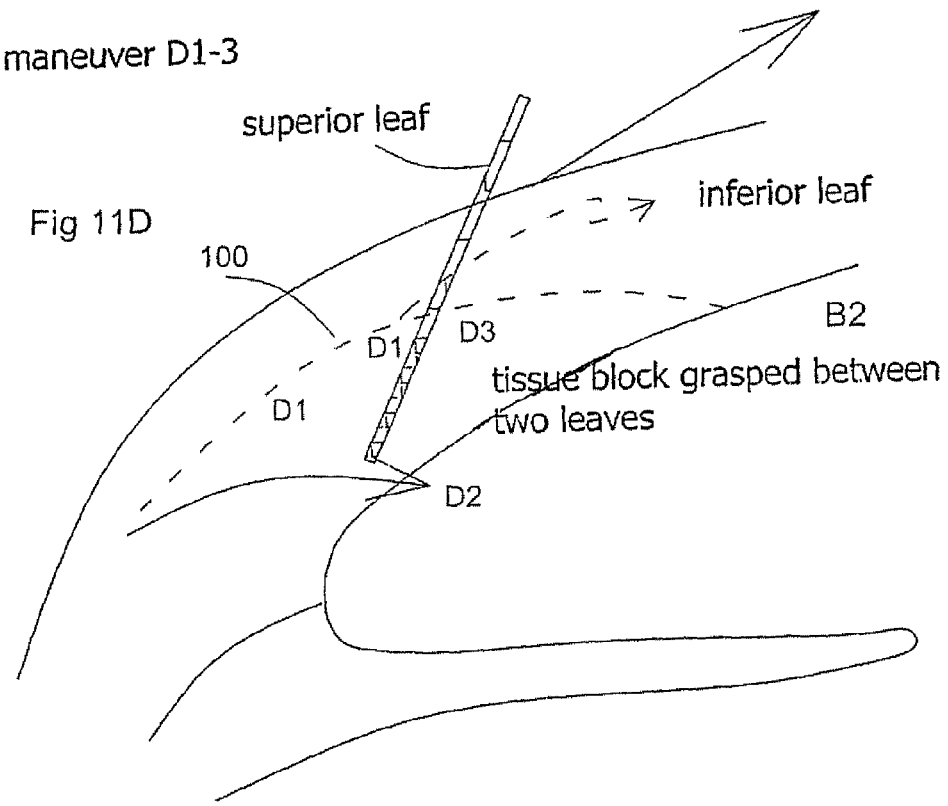
Figure 12D:
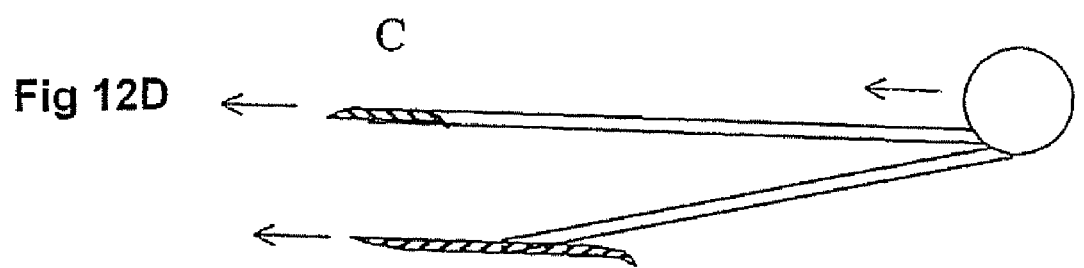

Next, tool 20 is again advanced along a path similar to its initial insertion path as shown in FIG. 11C. In this case, first blade element 28 follows a path $C_1$ substantially the same as initial path $A_1$. Second blade element 46, on the other hand, is now located on the inner side of the tissue wall and advances along a path $C_2$. In the case of the preferred ocular application, this movement brings second blade element 46 into engagement with tissue at or near the angle of the eye where an additional slit $C_2$ is cut, thereby defining including a region of trabecular tissue within the block cut. It is this cut which is particularly critical in defining the parameters of the surgical treatment for glaucoma in ocular applications. This tool movement is shown in FIG. 12D.

Figure 12E:
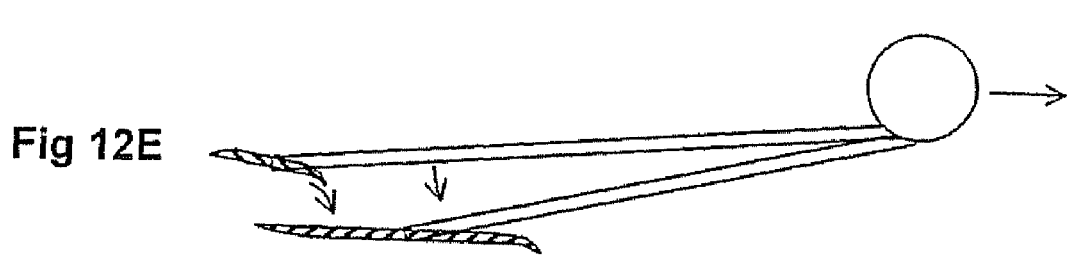

Finally, as shown in FIG. 11D, the tool is again withdrawn, this time with a downward levering motion and a bias applied towards its closed position. This results in the deflection feature 36 of first blade element 28 becoming lodged in the tissue of the first elongated slit so as to cut a third slit diverging from the first slit so as to form a distal cut of the tissue block. This tool motion is illustrated in FIG. 12E. The closing action of the tool also serves to grasp the cut tissue block between the two blade assemblies. The block is then typically withdrawn by pulling the tool together with the included tissue block out along the first elongated slit. The elasticity of the tissue is typically such that the tool and contained block pass relatively easily by temporary stretching of the tissue. After removal of the tool, the tissue returns resiliently to its relaxed state in which self-sealing flap 100 provides a seal against fluid leakage.

Figure 13:
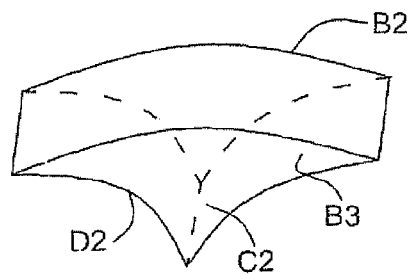
FIG. 13 is a schematic isometric view of a block of tissue cut by the method of FIGS. 11A-11D.

FIG. 13 shows a typical form of the tissue block cut by the preferred implementation of the present invention. The various faces of the block are labeled here with the corresponding letters used to designate the cuts of FIGS. 11A-D. The surface labeled $C_2$ corresponds in part to the natural inner surface of the cornea.

Turning now to the second preferred embodiment of the present invention, surgical tool 120 will be described with reference to FIGS. 14-22. Generally speaking, tool 120 bears a number of structural similarities to tool 20 described above and performs an almost identical sequence of incisions. A number of significant structural differences, however, render the structure of tool 120 particularly simple to manufacture and to operate.

Figure 14:
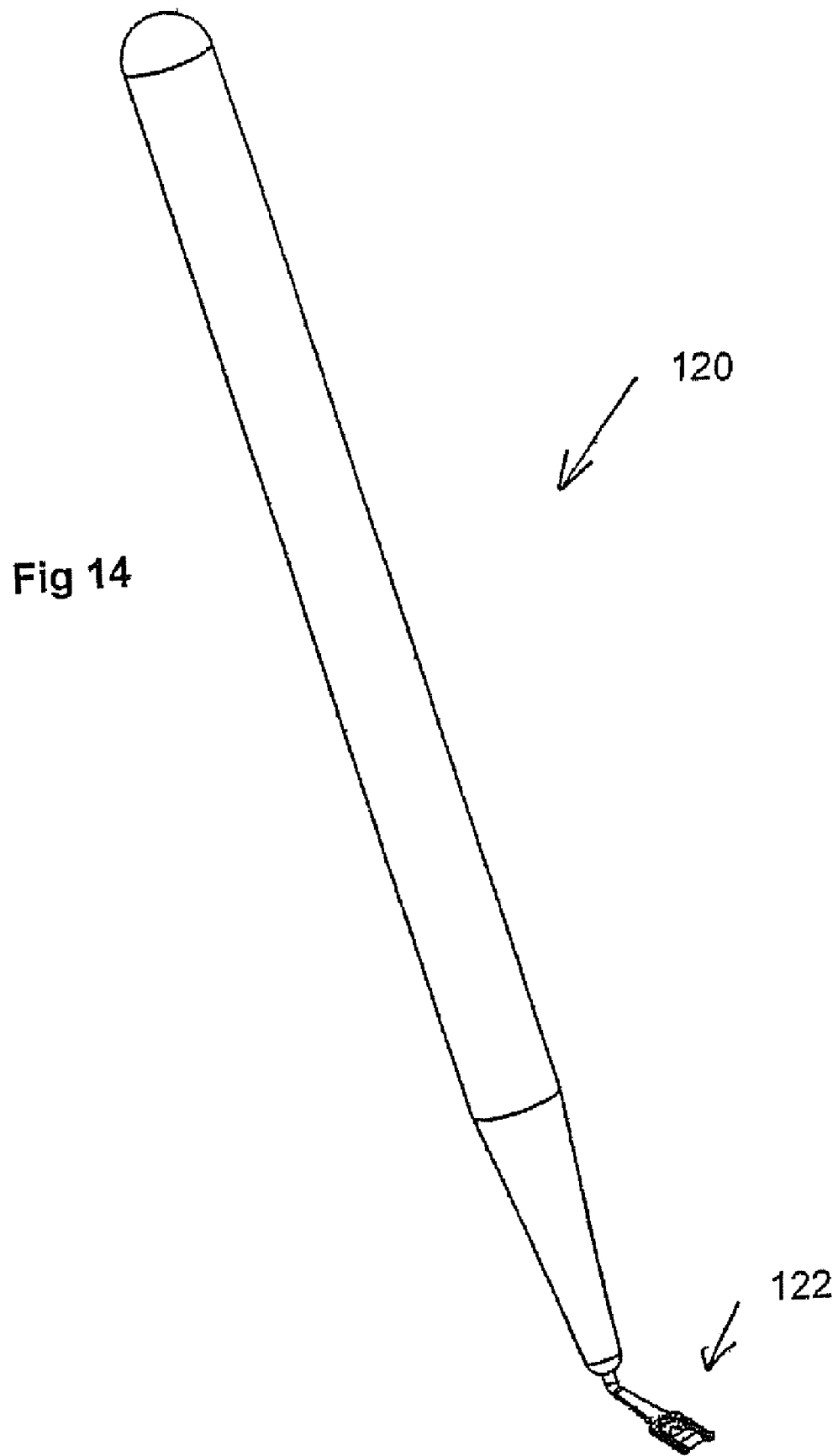
FIG. 14 is an isometric view of a second preferred embodiment of a surgical tool, constructed and operative according to the teachings of the present invention, for forming a self-sealing flap in tissue of a wall of a hollow organ and extracting a tissue block from the wall.

Turning now to the structure of tool 120, FIG. 14 shows a handle terminating in a tool head 122. Tool head 122, of which the structure and components are better seen in FIGS. 15-21, includes an elongated support element 124 having a direction of elongation 126. Support element 124, which is typically a forked formation similar to element 24 or 42 described above, is configured for insertion along a first slit parallel to the direction of elongation 126 into the tissue of the wall. A proximal (as held) or posterior (as inserted) blade element 128 is pivotally mounted on support element 124 so as to be pivotable about an axis 130 perpendicular to direction of elongation 126. Blade element 128 includes a rear blade 132 with at least one deflecting feature 134 configured for forming a second slit diverging from the first slit during withdrawal of the tool along the first slit, thereby forming a self-sealing flap in the tissue of the wall.

Figure 17:
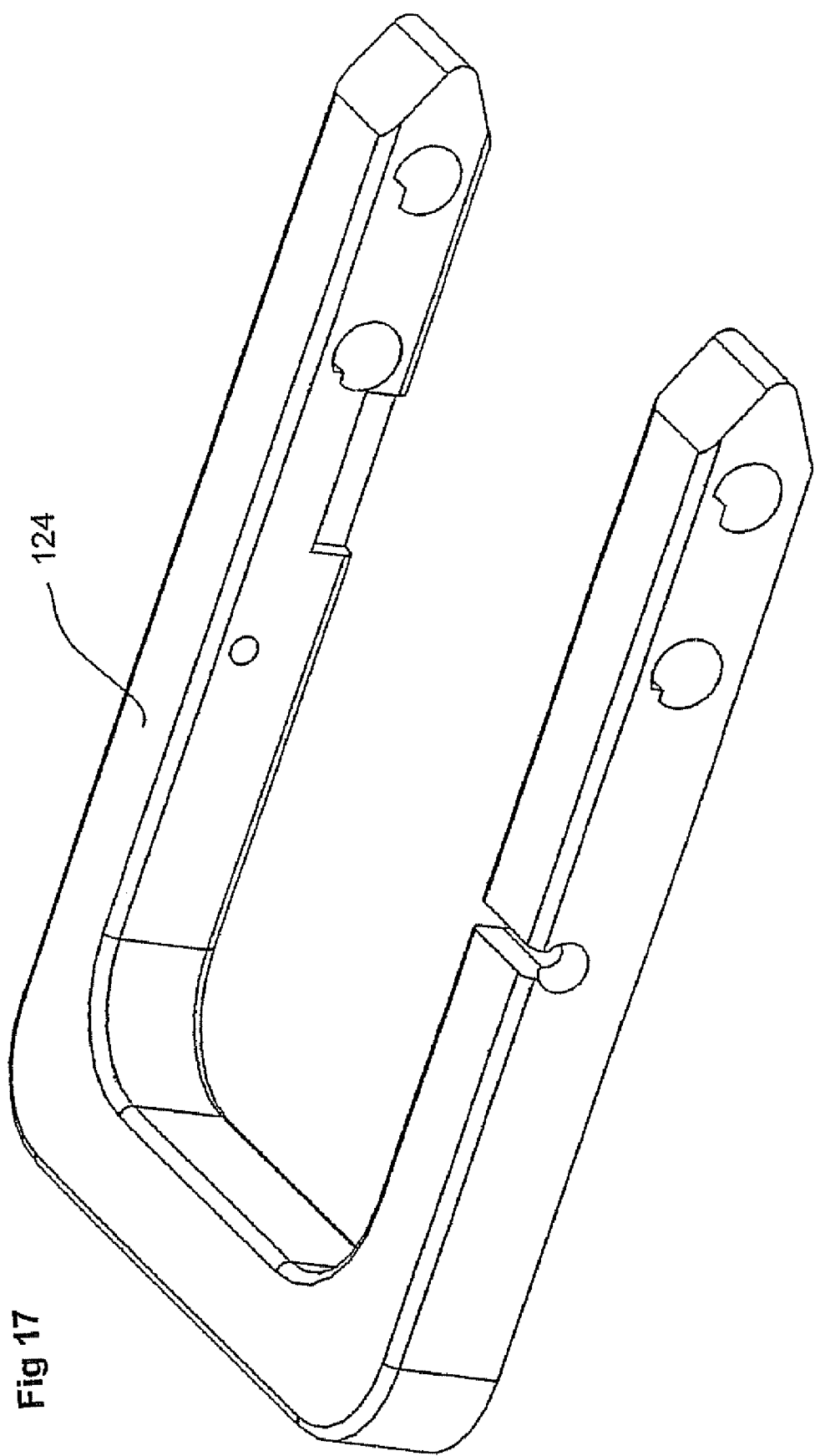
FIG. 17 is an isometric view of an elongated support element from the tool head of FIG. 15.
Figure 18:
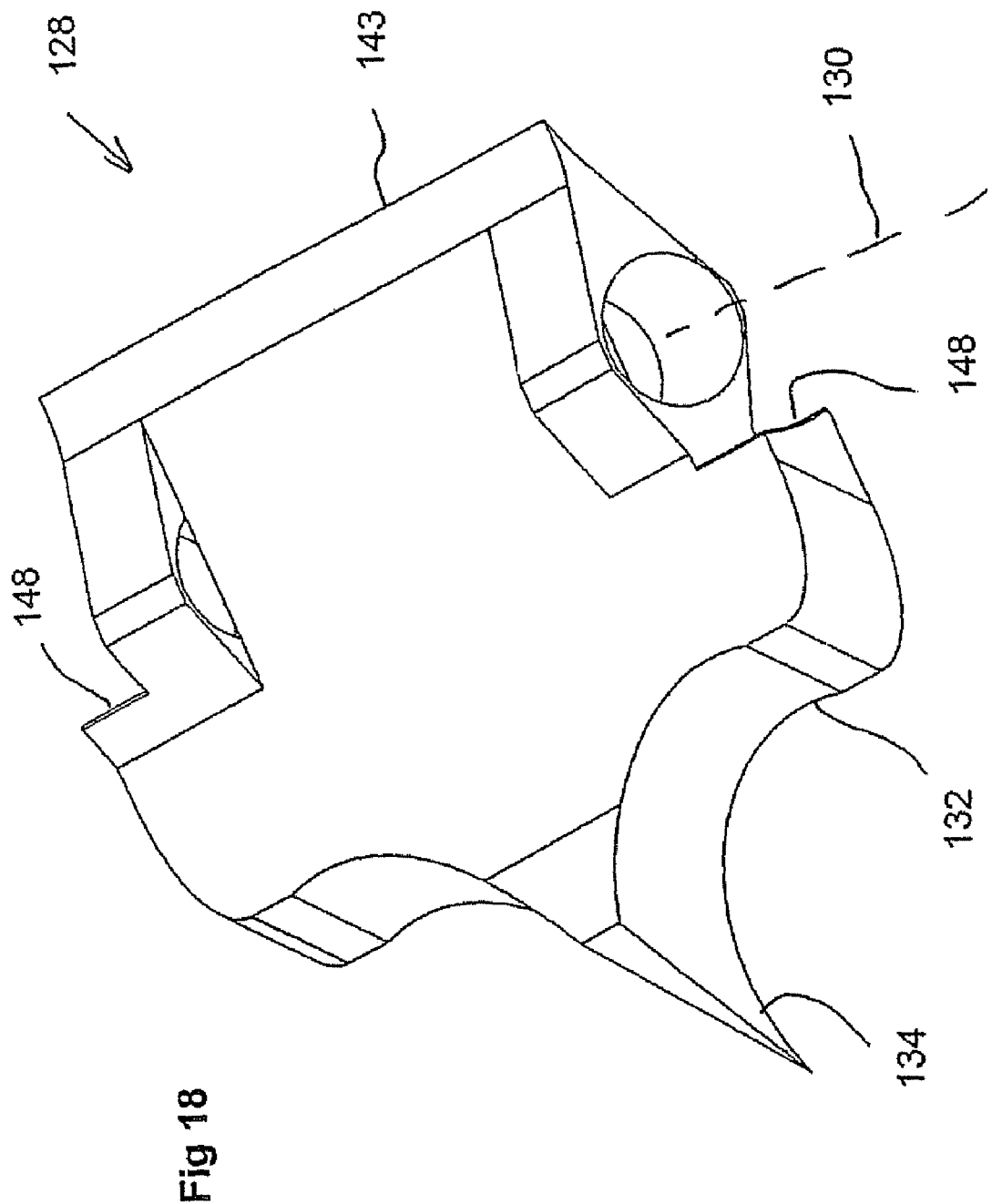
FIG. 18 is an isometric view of a posterior blade element from the tool head of FIG. 15.
Figure 19:
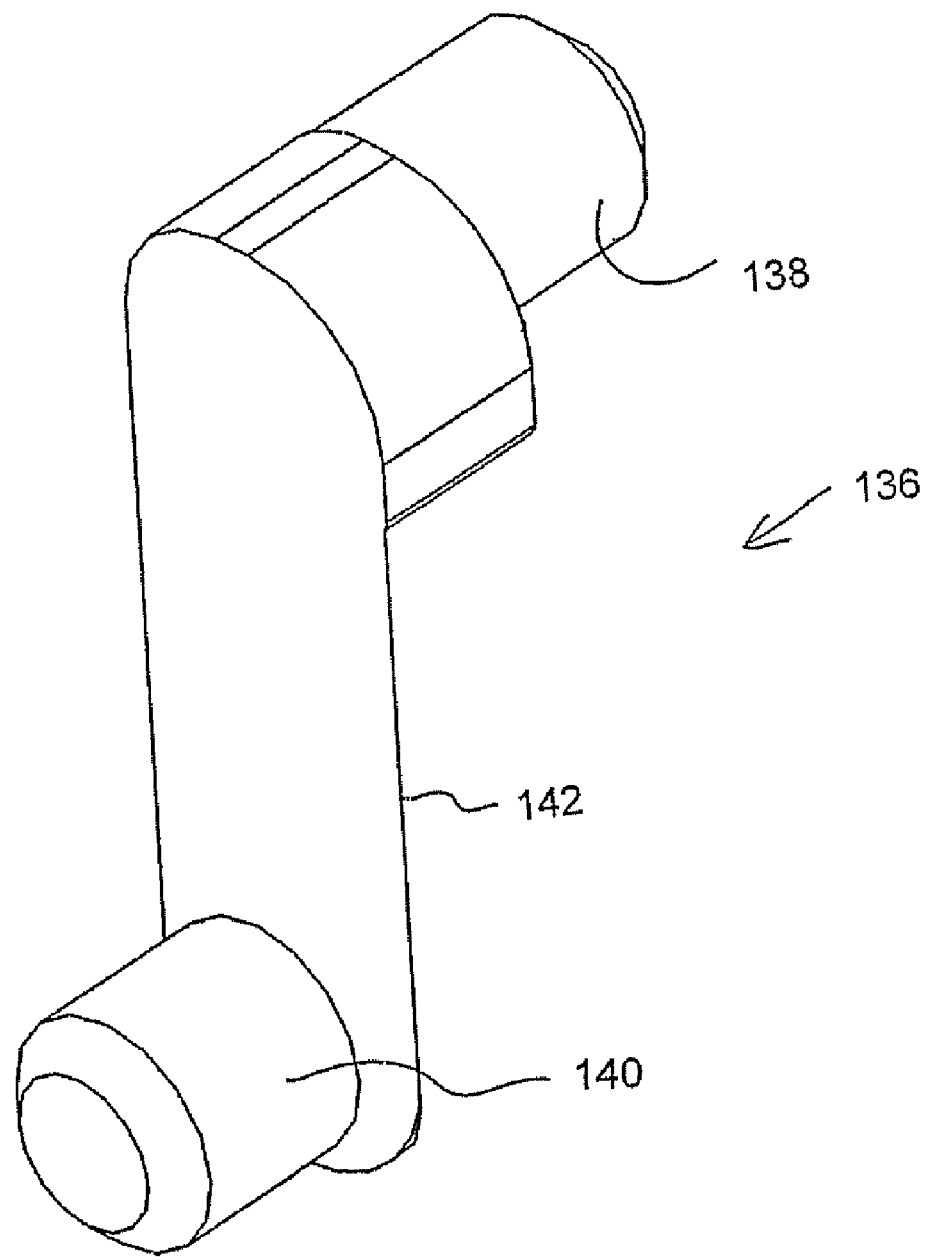
FIG. 19 is a front isometric view of a lever arm from the tool head of FIG. 15.
Figure 20:
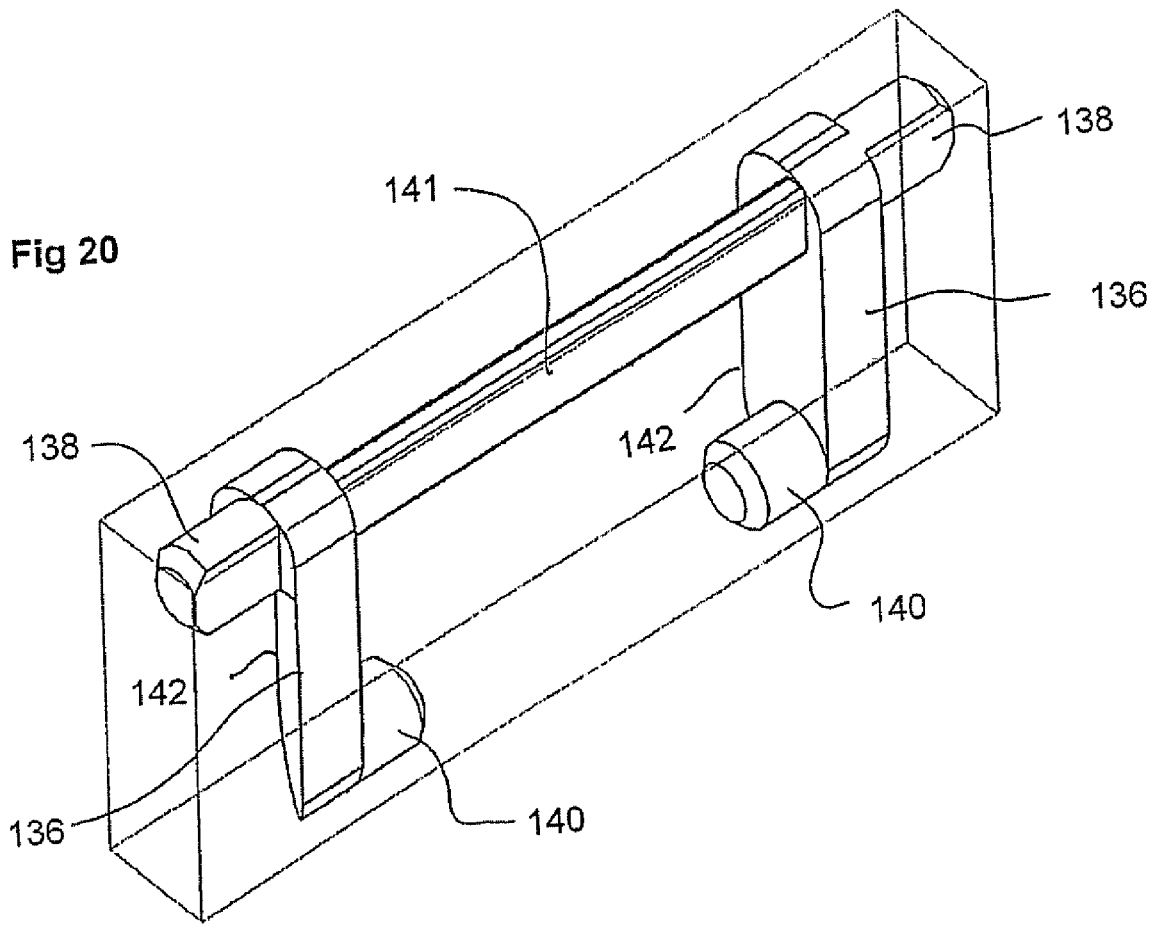
FIG. 20 is an isometric view of a lever mechanism from the tool head of FIG. 15, the mechanism including two lever arms similar to that of FIG. 19.
Figure 21:
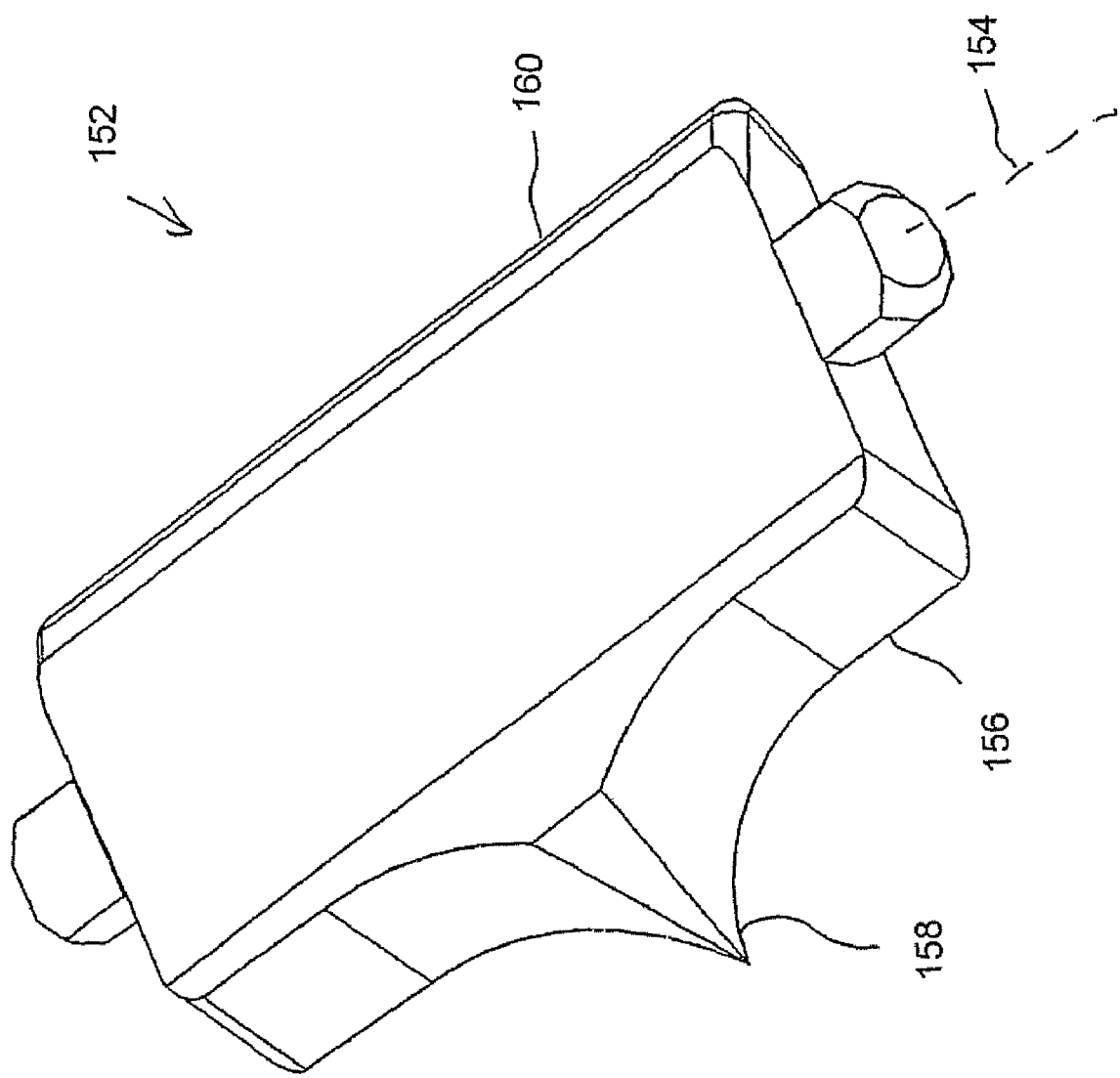
FIG. 21 is an isometric view of an anterior blade element from the tool head of FIG. 15.

Unlike tool 20, blade element 128 is here preferably mounted on support element 124 via a lever mechanism which is configured to allow displacement of blade element from an "in-plane" position (FIG. 16) to an "out-of-plane" position (FIG. 17). The terms "in-plane" and "out-of-plane" are used here to refer to the position of axis 130 relative to a "tool plane" passing through support element 128 and parallel to both direction of elongation 126 and axis 130. Thus, in the "in-plane" position, axis 130 lies substantially within the tool plane whereas, in the "out-of-plane" position, axis 130 is displaced so as to be parallel to, but removed from, the tool plane.

In the preferred implementation shown here, the lever mechanism is implemented using a pair of lever arms 136 each having a first end 138 pivotally engaged with support element 124 and a second end 140 pivotally engaged with blade element 128. The lever arms are preferably interconnected by a retention element in the form of a bar 141. The structure and function of bar 141 will be described further below.

Each lever arm 136 is preferably configured such that, when blade element 128 assumes its out-of-plane position, a distal edge of the lever arms presents a blade edge 142 extending substantially perpendicular to the tool plane and oriented for cutting parallel to direction of elongation 126. Blade element 128 also preferably includes a front blade 143 configured for cutting a slit parallel to the tool plane during advancing of the tool along the first slit. The function of these blades will be described further in the context of FIGS. 22C and 22D below.

Preferably, the position of lever arms 136 in the out-of-plane position is substantially perpendicular to the tool plane. A lock element 144 (best seen in FIG. 16) is preferably deployed to retain blade element 128 in the out-of-plane position once opened. This may be implemented simply as shown here as a resilient tab 144 which lodges behind one or both of the lever arms as they rotate to their open positions.

Figure 15:
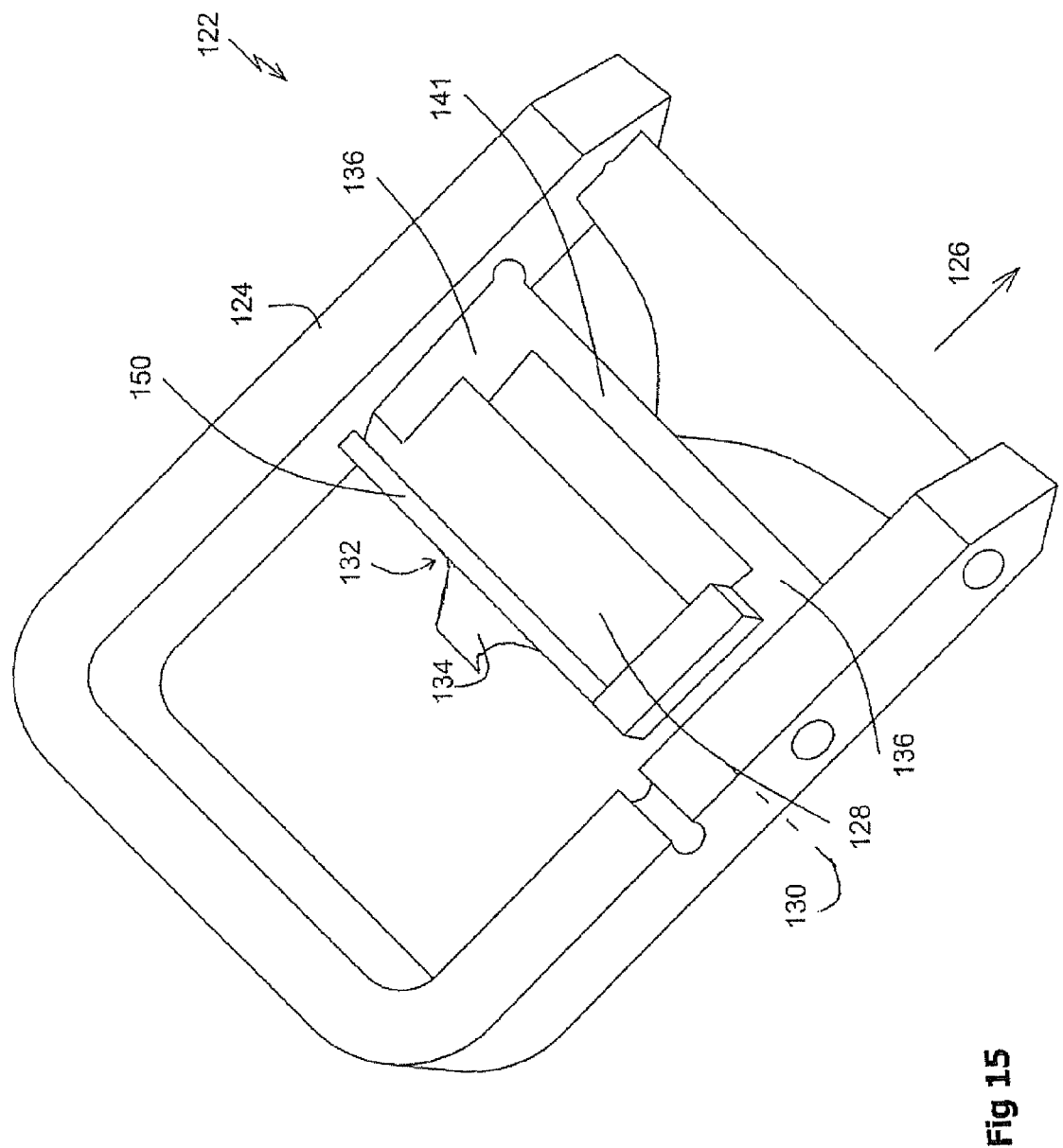
FIG. 15 is an enlarged isometric view of a distal tool head of the tool of FIG. 14 with the tool head in a closed state.
Figure 16:
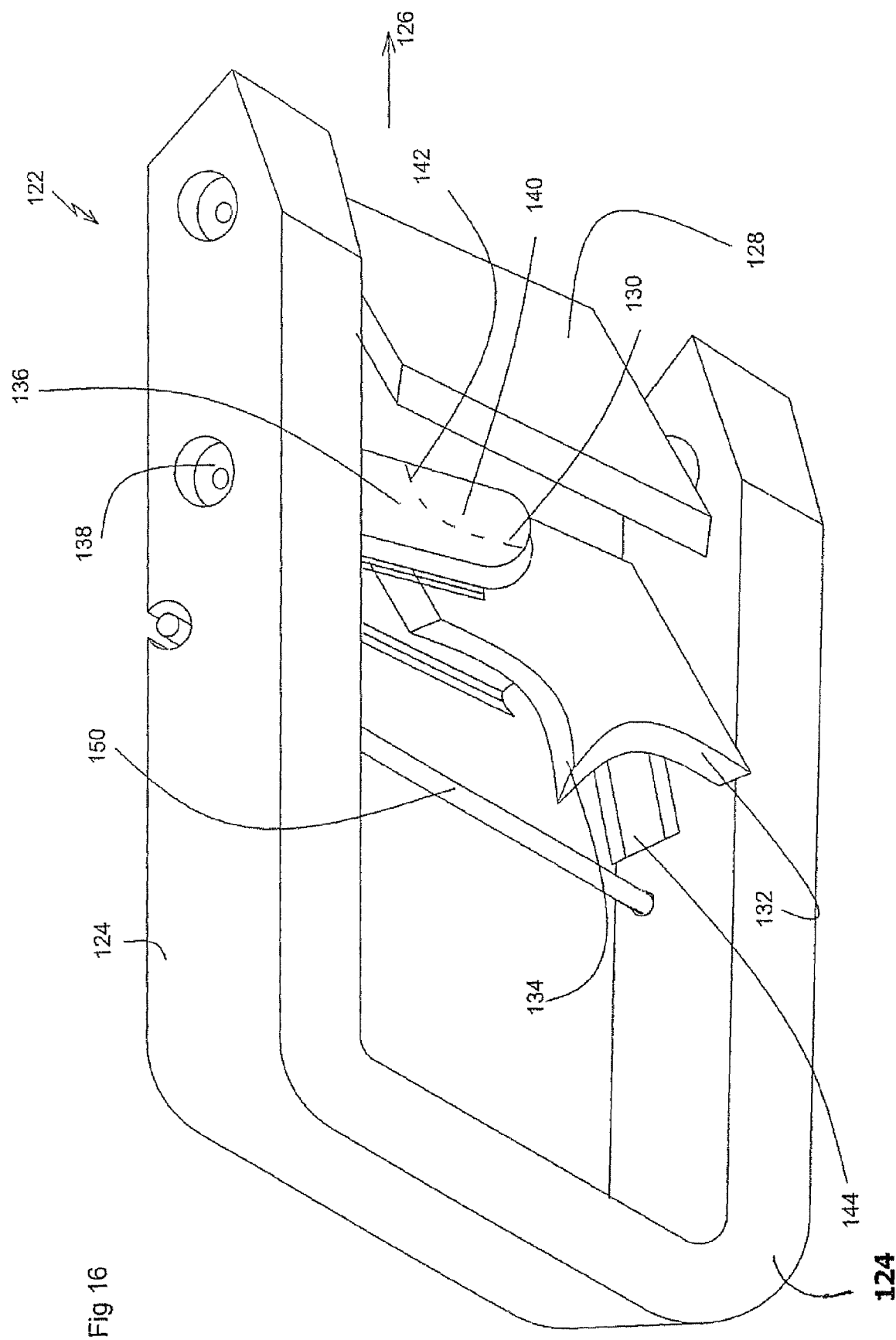
FIG. 16 is a lower isometric view of the tool head of FIG. 15 in an open state.

A further preferred feature of tool 120 is a resilient biasing element 146 associated with the lever mechanism and deployed such that, when blade element 128 assumes its out-of-plane position, biasing element 146 biases blade element 128 to a position with the main generally-flat portion of its upper surface substantially parallel to the tool plane. In the implementation illustrated here, resilient element 146 is implemented as a leaf spring which is initially held in a curved form between the rounded bottom end of lever arm 136 and an opposing concave facet 148 of blade element 128. The leaf spring is biased to tend to return to a straight configuration so that, when the blade element is lowered to the out-of-plane position and is not otherwise restrained, the blade element is brought to the aforementioned parallel orientation. In the initial in-plane position, blade element 128 is prevented from flipping upwards by a crossbar 150 as seen in FIG. 15. Preferably, crossbar 150 also serves a locking function during assembly of tool 120 by fixing the distance between sides of the fork assembly so that the elements inserted between them by outward flexing of the fork structure cannot subsequently slip out.

Finally, tool 120 also preferably includes a distal (anterior) blade element 152 pivotally mounted on support element 124 distally with respect to blade element 128. Distal blade element 152 is pivotable about a second axis 154 parallel to axis 130. Blade element 152 has a rear blade 156 with at least one deflecting feature 158 configured for forming an additional slit diverging from the first slit during withdrawal of the tool along the first slit. The front edge 160 of distal blade element 152 is most preferably rounded so as not to unintentionally extend the first slit beyond a precut length.

In order to prevent premature rotation of distal blade element 152 about its axis 154, the tool head structure is preferably configured such that pivotal movement of blade element 152 is limited at least until proximal blade element 128 moves out of its in-plane position. In the example shown here, this is achieved by abutment between a surface of blade element 152 and a retention element (aforementioned retention bar 141) as will now be described in the context of operation of tool 120.

Turning now to the sequence of operation of tool 120, it is a preferred feature of the method of the present invention as performed by this embodiment that the initial slit for insertion of the tool is performed by a separate surgical tool (not shown) prior to insertion of tool 120, while the front edge of distal blade element 152 and the ends of support element 124 are rounded to avoid unintended elongation of the slit. This allows exact predetermination of the extent of the incision using conventional techniques, thereby rendering the subsequent procedure less delicate.

After cutting the initial slit, tool head 112 is preferably fully inserted along the slit while covered by a protective sleeve, such as of Teflon, which is then withdrawn. The resulting initial placement of tool head 112 is then as represented in FIG. 22A. The tool is then withdrawn (i.e., to the right as shown). During this motion, the deflecting feature 134 of proximal blade 128 becomes lodged in the tissue and guides rear blade 132 downwards to for an undercut slit as shown in FIG. 22B, thereby creating a small-angle self-sealing tissue flap as described in the first embodiment. The motion also draws down lever arms 136 with blade element 128 as shown. As the rearward motion continues, the tissue at the sides of the slit applies pressure to the flat rear edges of the lever arms, thereby tending to open them further. This effect combined with the effect of biasing element 146 ensure that, when blade element 128 penetrates the inner surface of the tissue, lever arms 136 swing to their perpendicular open positions and blade element 128 return to their orientation parallel to the tool plane as shown in FIG. 22C. From this point on, lever arms 136 are locked in this open position by lock elements 144.

Parenthetically, the operation of retention bar 141 is also clearly illustrated by FIGS. 22A-22C. Initially, the rear blade of distal blade element 152 is lodged above bar 141. This prevents blade element 152 from cutting into the underlying tissue during the withdrawal motion described. As lever arms 136 swing down, the eccentrically mounted retention bar 141 shifts until, near the fully open position, it clears blade element 152, thereby allowing pivotal motion.

The next step is a second forward movement. This time, as support element 124 advances along the first slit, blade edges 142 of lever arms 136 cut side faces of the tissue block. Similarly, when front blade 143 of blade element 128 encounters tissue (e.g. at the angle of the eye), it continues into the tissue, cutting a lower surface of the tissue block. This movement continues until the blunt end of support element 124 and/or the rounded front edge 160 of distal blade 152 reaches the predefined end of the first slit.

The tool is then withdrawn a second time along the first slot. This time, distal blade element 152 is clear of retention bar 141 and is therefore free to pivot. As a result, deflecting feature 158 becomes lodged in the tissue as shown in FIG. 22D and deflects blade element 152 downwards to cut a distal surface of the tissue block. The substantially severed tissue block is then substantially contained by distal blade element 152 at its distal end, by proximal blade element 128 from below, by lever arms 136 at the sides, and by retention bar 141 and crossbar 150 from above. Tool 120 is then withdrawn (by temporary stretching of the tissue) along the insertion slot with the tissue block retained therein. On removal of the tool, the tissue springs back to its undeformed state in which the small-angle flap seals the incision.

Preferably, a shoehorn-shaped tool (not shown) is inserted along the first slit underneath tool 120 prior to its final withdrawal so as to minimize abrasive irritation or damage to the tissue along the faces of the slot.

A range of further modifications to the device of the present invention will be clear to one ordinarily skilled in the art. For example, the device may be modified by wiring to an external remote electrical power source as is known in the art to perform local cauterization of cut tissue by heating of part or all of one or more blades during or subsequent to the cutting operations.

It will be appreciated that the above descriptions are intended only to serve as examples, and that many other embodiments are possible within the broad scope of the present invention as defined by the appended claims

What is claimed is:

1. A surgical tool for forming a self-sealing flap in tissue of a wall of a hollow organ during a procedure for extracting a tissue block from the wall, the surgical tool comprising a tool head including:
   (a) an elongated support element having a direction of elongation and configured for insertion along a first slit parallel to said direction of elongation into the tissue of the wall;
   (b) a blade element pivotally mounted on said support element so as to be pivotable about an axis perpendicular to said direction of elongation, said blade element including a rear blade with at least one deflecting feature configured for forming a second slit diverging from said first slit during withdrawal of the tool along the first slit, thereby forming a self-sealing flap in the tissue of the wall;
   wherein a plane passing through said support element parallel to both said direction of elongation and said axis is referred to as a tool plane, and wherein said blade element is mounted on said support element via a lever mechanism, said lever mechanism being configured to allow displacement of said blade element from an in-plane position in which said axis lies substantially within said tool plane to an out-of-plane position in which said axis is displaced so as to be parallel to, but removed from, said tool plane; and
   wherein said lever mechanism includes a pair of lever arms each having a first end pivotally engaged with said support and a second end pivotally engaged with said blade element.

2. The surgical tool of claim 1, wherein said lever arms are configured such that, when said blade element assumes said out-of-plane position, at least part of each of said lever arms presents a blade edge extending substantially perpendicular to said tool plane and oriented for cutting parallel to said direction of elongation.

3. The surgical tool of claim 1, wherein said lever mechanism further includes a lock element configured to retain said blade element in said out-of-plane position.

4. The surgical tool of claim 3, wherein said blade element has a substantially planar upper surface, the lever mechanism further including a resilient biasing element deployed such that, when said blade element assumes said out-of-plane position, said biasing element biases said blade element to a position with said upper surface substantially parallel to said tool plane.

5. The surgical tool of claim 4, wherein said blade element further includes a front blade configured for cutting a slit parallel to said tool plane during advancing of the tool along the first slit.

6. The surgical tool of claim 5, wherein said blade element is referred to as said first blade element, and wherein said axis is referred to as said first axis, the tool head further including a second blade element pivotally mounted on said support element distally with respect to said first blade element, said second blade element being pivotable about a second axis parallel to said first axis, said second blade element including a rear blade with at least one deflecting feature configured for forming an additional slit diverging from said first slit during withdrawal of the tool along the first slit.

7. The surgical tool of claim 6, wherein said lever mechanism further includes a retention element deployed such that, when said blade element assumes said in-plane position, said retention element abuts a surface of said second blade element so as to limit pivotal movement of said second blade element about said second axis and, when said blade element assumes said out-of-plane position, said retention element is removed from said second blade element so as not to limit pivotal movement of said second blade element about said second axis.

8. The surgical tool of claim 1, wherein said elongated support element includes a fork portion formed with two projecting arms, said blade element being mounted between said projecting arms.

9. The surgical tool of claim 8, wherein a distal portion of each of said projecting arms is formed as a blade parallel to said direction of elongation.

10. The surgical tool of claim 1, wherein said blade element further includes a pair of side blades extending along a majority of a length between a front blade and a rear blade in a direction substantially perpendicular to said axis.

11. The surgical tool of claim 10, wherein said blade element further includes an opening substantially circumscribed by said front blade, said rear blade and said pair of side blades.

12. The surgical tool of claim 1, further comprising a blade control assembly including at least one abutment element mechanically interconnected with said elongated support element so as to be movable relative to said elongated support element between a closed position in which said at least one abutment element abuts said blade element so as to restrain pivotal movement of said blade element and an open position in which said abutment element is removed from said blade element so as to allow pivotal movement of said blade element.

13. The surgical tool of claim 12, wherein said at least one abutment element is implemented as a second blade assembly including:
   (a) a second elongated support element having a second direction of elongation; and
   (b) a second blade element pivotally mounted on said second support element so as to be pivotable about a second axis perpendicular to said second direction of elongation.

14. The surgical tool of claim 13, wherein said second blade element includes a second front blade configured for cutting a primary slit parallel to said second axis during advancing of the tool into the tissue of the wall, and a second rear blade with at least one deflecting feature configured for forming a secondary slit diverging from said primary slit during withdrawal of the tool along the first slit.

15. The surgical tool of claim 13, wherein said second blade element is restrained from pivotal movement when said second blade assembly assumes said closed position.

16. The surgical tool of claim 13, wherein said second blade assembly is resiliently biased towards said open position.

17. A surgical tool for forming a self-sealing flap in tissue of a wall of a hollow organ and extracting a tissue block from the wall, the surgical tool comprising:
   (a) a first blade assembly including:
      (i) a first elongated support element having a first direction of elongation, and
      (ii) a first blade element pivotally mounted on said first support element so as to be pivotable about a first axis perpendicular to said first direction of elongation, said first blade element including a first front blade configured for cutting a first forward slit parallel to said first axis during advancing of the tool, and a first rear blade with at least one deflecting feature configured for forming a first reverse slit diverging from said first forward slit during withdrawal of the tool along the first forward slit;
   (b) a second blade assembly including:
      (i) a second elongated support element having a second direction of elongation, and
      (ii) a second blade element pivotally mounted on said second support element so as to be pivotable about a second axis perpendicular to said second direction of elongation, said second blade element including a second front blade configured for cutting a second forward slit parallel to said second axis during advancing of the tool, and a second rear blade with at least one deflecting feature configured for forming a second reverse slit diverging from said second forward slit during withdrawal of the tool along the second forward slit; and
   (c) a mechanical linkage interconnecting between said first elongated support element and said second elongated support element so as to define a range of relative movement between a closed position in which said first blade assembly is closed against said second blade assembly and an open position in which said first blade assembly and said second blade assembly are spaced apart.

18. The surgical tool of claim 17, wherein said first blade assembly and said second blade assembly are configured such that, when in said closed position, said first blade element and said second blade element are restrained against pivotal movement.

19. The surgical tool of claim 17, wherein each of said first elongated support element and said second elongated support element includes a fork portion formed with two projecting arms, said first and second blade elements being mounted between said projecting arms.

20. The surgical tool of claim 19, wherein a distal portion of each of said projecting arms is formed as a blade parallel to said direction of elongation.

21. The surgical tool of claim 17, wherein said blade element further includes a pair of side blades extending along a majority of a length between at least one of said front blades and at least one of said rear blades in a direction substantially perpendicular to said axis.

22. The surgical tool of claim 21, wherein said blade element further includes an opening substantially circumscribed by at least one of said front blades, at least one of said rear blades and said pair of side blades.

* * * * *